(12) United States Patent
Li et al.

(10) Patent No.: US 7,754,745 B2
(45) Date of Patent: *Jul. 13, 2010

(54) AZACYCLOPENTANE DERIVATIVES AS INHIBITORS OF STEAROYL-COENZYME A DELTA-9 DESATURASE

(75) Inventors: Chun Sing Li, Dollard-des-Ormeaux (CA); Yeeman K. Ramtohul, Pierrefonds (CA)

(73) Assignee: Merck Frosst Canada Ltd., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/227,549

(22) PCT Filed: Jun. 8, 2007

(86) PCT No.: PCT/CA2007/001027

§ 371 (c)(1),
(2), (4) Date: Nov. 20, 2008

(87) PCT Pub. No.: WO2007/143824

PCT Pub. Date: Dec. 21, 2007

(65) Prior Publication Data

US 2009/0093527 A1    Apr. 9, 2009

Related U.S. Application Data

(60) Provisional application No. 60/813,091, filed on Jun. 13, 2006.

(51) Int. Cl.
*C07D 417/04* (2006.01)
*A61K 31/433* (2006.01)
*A61K 31/427* (2006.01)

(52) U.S. Cl. .................. 514/363; 548/131; 548/138; 548/190; 514/364; 514/370

(58) Field of Classification Search .................. 548/193
See application file for complete search history.

(56) References Cited

U.S. PATENT DOCUMENTS

| | | | | |
|---|---|---|---|---|
| 5,266,582 | A * | 11/1993 | de Nanteuil et al. | 514/367 |
| 7,557,131 | B2 * | 7/2009 | Brown et al. | 514/340 |
| 2007/0010511 | A1 * | 1/2007 | Herold et al. | 514/227.8 |
| 2008/0132542 | A1 | 6/2008 | Lachance et al. | |
| 2008/0182838 | A1 | 7/2008 | Leblanc et al. | |

FOREIGN PATENT DOCUMENTS

| | | |
|---|---|---|
| CA | 2 577 061 A1 | 3/2006 |
| CA | 2 580 844 A1 | 3/2006 |
| CA | 2 580 855 A1 | 3/2006 |
| WO | WO 2005/092890 A2 | 10/2005 |
| WO | WO 2005/092890 A3 | 10/2005 |
| WO | WO 2006034440 A2 * | 3/2006 |
| WO | WO 2006/130986 A1 | 12/2006 |
| WO | WO 2007/009236 A1 | 1/2007 |
| WO | WO 2007/046868 A2 | 4/2007 |
| WO | WO 2007/046868 A3 | 4/2007 |
| WO | WO 2007/056846 A1 | 5/2007 |
| WO | WO 2007/071023 A1 | 6/2007 |
| WO | WO 2007/134457 A1 | 11/2007 |
| WO | WO 2007/143823 A1 | 12/2007 |
| WO | WO 2007/143824 A1 | 12/2007 |
| WO | WO 2008/017161 A1 | 2/2008 |
| WO | WO 2008/046226 A1 | 4/2008 |
| WO | WO 2008/064474 A1 | 6/2008 |
| WO | WO 2008/089580 A1 | 7/2008 |
| WO | WO 2008/141455 A1 | 11/2008 |

OTHER PUBLICATIONS de Nanteuil et al. Arzneimittel-Forschung (1995), 45(11), 1176-81.*

* cited by examiner

*Primary Examiner*—Rebecca L Anderson
*Assistant Examiner*—Matthew P Coughlin
(74) *Attorney, Agent, or Firm*—Philippe L. Derette; John C. Todaro

(57) ABSTRACT

Azacyclopentane derivatives of structural formula (I) are selective inhibitors of stearoyl-coenzyme A delta-9 desaturase (SCD1) relative to other known stearoyl-coenzyme A desaturases. The compounds of the present invention are useful for the prevention and treatment of conditions related to abnormal lipid synthesis and metabolism, including cardiovascular disease; atherosclerosis; obesity; diabetes; neurological disease; metabolic syndrome; insulin resistance; liver steatosis; and non-alcoholic steatohepatitis.

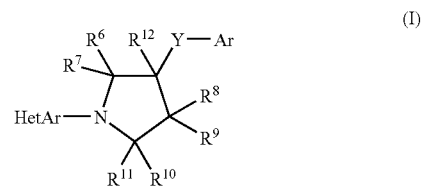

15 Claims, No Drawings

AZACYCLOPENTANE DERIVATIVES AS INHIBITORS OF STEAROYL-COENZYME A DELTA-9 DESATURASE

CROSS REFERENCE TO RELATED APPLICATIONS

This application is the National Stage of International Application No. PCT/CA2007/001027, filed 8 Jun. 2007, which claims the benefit under 35 U.S.C. 119(e) of U.S. Provisional Application No. 60/813,091, filed 13 Jun. 2006.

FIELD OF THE INVENTION

The present invention relates to azacyclopentane derivatives which are inhibitors of stearoyl-coenzyme A delta-9 desaturase (SCD) and the use of such compounds to control, prevent and/or treat conditions or diseases mediated by SCD activity. The compounds of the present invention are useful for the control, prevention and treatment of conditions and diseases related to abnormal lipid synthesis and metabolism, including cardiovascular disease; atherosclerosis; obesity; diabetes; neurological disease; metabolic syndrome; insulin resistance; cancer; liver steatosis; and non-alcoholic steatohepatitis.

BACKGROUND OF THE INVENTION

At least three classes of fatty acyl-coenzyme A (CoA) desaturases (delta-5, delta-6 and delta-9 desaturases) are responsible for the formation of double bonds in mono- and polyunsaturated fatty acyl-CoAs derived from either dietary sources or de novo synthesis in mammals. The delta-9 specific stearoyl-CoA desaturases (SCDs) catalyze the rate-limiting formation of the cis-double bond at the C9-C10 position in monounsaturated fatty acyl-CoAs. The preferred substrates are stearoyl-CoA and palmitoyl-CoA, with the resulting oleoyl and palmitoleoyl-CoA as the main components in the biosynthesis of phospholipids, triglycerides, cholesterol esters and wax esters (Dobrzyn and Natami, *Obesity Reviews*, 6: 169-174 (2005)).

The rat liver microsomal SCD protein was first isolated and characterized in 1974 (Strittmatter et al., *PNAS*, 71: 4565-4569 (1974)). A number of mammalian SCD genes have since been cloned and studied from various species. For example, two genes have been identified from rat (SCD1 and SCD2, Thiede et al., *J. Biol. Chem.*, 261, 13230-13235 (1986)), Mihara, K., *J. Biochem. (Tokyo)*, 108: 1022-1029 (1990)); four genes from mouse (SCD1, SCD2, SCD3 and SCD4) (Miyazaki et al., *J. Biol. Chem.*, 278: 33904-33911 (2003)); and two genes from human (SCD1 and ACOD4 (SCD2)), (Zhang, et al., *Biochem. J.*, 340: 255-264 (1991); Beiraghi, et al., *Gene*, 309: 11-21 (2003); Zhang et al., *Biochem. J.*, 388: 135-142 (2005)). The involvement of SCDs in fatty acid metabolism has been known in rats and mice since the 1970's (Oshino, N., *Arch. Biochem. Biophys.*, 149: 378-387 (1972)). This has been further supported by the biological studies of a) Asebia mice that carry the natural mutation in the SCD1 gene (Zheng et al., *Nature Genetics*, 23: 268-270 (1999)), b) SCD1-null mice from targeted gene deletion (Ntambi, et al., *PNAS*, 99: 11482-11486 (2002), and c) the suppression of SCD1 expression during leptin-induced weight loss (Cohen et al., *Science*, 297: 240-243 (2002)). The potential benefits of pharmacological inhibition of SCD activity has been demonstrated with anti-sense oligonucleotide inhibitors (ASO) in mice (Jiang, et al., *J. Clin. Invest.*, 115: 1030-1038 (2005)). ASO inhibition of SCD activity reduced fatty acid synthesis and increased fatty acid oxidation in primary mouse hepatocytes. Treatment of mice with SCD-ASOs resulted in the prevention of diet-induced obesity, reduced body adiposity, hepatomegaly, steatosis, postprandial plasma insulin and glucose levels, reduced de novo fatty acid synthesis, decreased expression of lipogenic genes, and increased expression of genes promoting energy expenditure in liver and adipose tissues. Thus, SCD inhibition represents a novel therapeutic strategy in the treatment of obesity and related metabolic disorders.

There is compelling evidence to support that elevated SCD activity in humans is directly implicated in several common disease processes. For example, there is an elevated hepatic lipogenesis to triglyceride secretion in non-alcoholic fatty liver disease patients (Diraison, et al., *Diabetes Metabolism*, 29: 478-485 (2003)); Donnelly, et al., *J. Clin. Invest.*, 115: 1343-1351 (2005)). The postprandial de novo lipogenesis is significantly elevated in obese subjects (Marques-Lopes, et al., *American Journal of Clinical Nutrition*, 73: 252-261 (2001)). There is a significant correlation between a high SCD activity and an increased cardiovascular risk profile including elevated plasma triglycerides, a high body mass index and reduced plasma HDL (Attie, et al.,*J. Lipid Res.*, 43: 1899-1907 (2002)). SCD activity plays a key role in controlling the proliferation and survival of human transformed cells (Scaglia and Igal, *J. Biol. Chem.*, (2005)).

Other than the above mentioned anti-sense oligonucleotides, inhibitors of SCD activity include non-selective thia-fatty acid substrate analogs [B. Behrouzian and P. H. Buist, *Prostaglandins, Leukotrienes, and Essential Fatty Acids*, 68: 107-112 (2003)], cyclopropenoid fatty acids (Raju and Reiser, *J. Biol. Chem.*, 242: 379-384 (1967)), certain conjugated long-chain fatty acid isomers (Park, et al., *Biochim. Biophys. Acta*, 1486: 285-292 (2000)) and a series of pyridazine derivatives disclosed in published international patent applications WO 2005/011653, 2005/011654, 2005/011656, 2005/011656, and 2005/011657, all assigned to Xenon Pharmaceuticals, Inc.

The present invention is concerned with novel azacyclopentane derivatives as inhibitors of stearoyl-CoA delta-9 desaturase which are useful in the treatment and/or prevention of various conditions and diseases mediated by SCD activity including those related, but not limited, to elevated lipid levels, as exemplified in non-alcoholic fatty liver disease, cardiovascular disease, obesity, diabetes, metabolic syndrome, and insulin resistance.

The role of stearoyl-coenzyme A desaturase in lipid metabolism has been described by M. Miyazaki and J. M. Ntambi, *Prostaglandins, Leukotrienes, and Essential Fatty Acids*, 68: 113-121 (2003). The therapeutic potential of the pharmacological manipulation of SCD activity has been described by A. Dobryzn and J. M. Ntambi, in "Stearoyl-CoA desaturase as a new drug target for obesity treatment" *Obesity Reviews*, 6: 169-174 (2005).

SUMMARY OF THE INVENTION

The present invention relates to azacyclopentane derivatives of structural formula I:

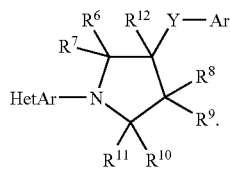

These azacyclopentane derivatives are effective as inhibitors of SCD. They are therefore useful for the treatment, control or prevention of disorders responsive to the inhibition of SCD, such as diabetes, insulin resistance, lipid disorders, obesity, atherosclerosis, and metabolic syndrome.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of SCD in a subject in need thereof by administering the compounds and pharmaceutical compositions of the present invention.

The present invention also relates to methods for the treatment, control, or prevention of Type 2 diabetes, insulin resistance, obesity, lipid disorders, atherosclerosis, and metabolic syndrome by administering the compounds and pharmaceutical compositions of the present invention.

The present invention also relates to methods for the treatment, control, or prevention of obesity by administering the compounds of the present invention in combination with a therapeutically effective amount of another agent known to be useful to treat the condition.

The present invention also relates to methods for the treatment, control, or prevention of Type 2 diabetes by administering the compounds of the present invention in combination with a therapeutically effective amount of another agent known to be useful to treat the condition.

The present invention also relates to methods for the treatment, control, or prevention of atherosclerosis by administering the compounds of the present invention in combination with a therapeutically effective amount of another agent known to be useful to treat the condition.

The present invention also relates to methods for the treatment, control, or prevention of lipid disorders by administering the compounds of the present invention in combination with a therapeutically effective amount of another agent known to be useful to treat the condition.

The present invention also relates to methods for treating metabolic syndrome by administering the compounds of the present invention in combination with a therapeutically effective amount of another agent known to be useful to treat the condition.

DETAILED DESCRIPTION OF THE INVENTION

The present invention is concerned with azacyclopentane derivatives useful as inhibitors of SCD. Compounds of the present invention are described by structural formula I:

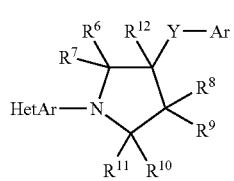

or a pharmaceutically acceptable salt thereof; wherein
Y is O, $S(O)_p$, or $CR^1R^2$;
Ar is phenyl, benzyl, naphthyl, or pyridyl each of which is optionally substituted with one to five substituents independently selected from $R^3$;

HetAr is an heteroaromatic ring selected from the group consisting of:
oxazolyl,
thiazolyl,
imidazolyl,
pyrazolyl,
isoxazolyl,
isothiazolyl,
1,2,4-oxadiazolyl,
1,3,4-oxadiazolyl,
1,2,5-oxadiazolyl,
1,2,3-oxadiazolyl,
1,2,4-thiadiazolyl,
1,2,5-thiadiazolyl,
1,3,4-thiadiazolyl,
1,2,3-thiadiazolyl,
1,2,4-triazolyl,
1,2,3-triazolyl,
tetrazolyl,
benzthiazolyl,
benzoxazolyl,
benzimidazolyl,
benzisoxazolyl, and
benzisothiazolyl;

in which the heteroaromatic ring is optionally substituted with one to two substituents independently selected from $R^5$;
$R^1$ and $R^2$ are each independently hydrogen or $C_{1-3}$ alkyl, wherein alkyl is optionally substituted with one to three substituents independently selected from fluorine and hydroxy;
each $R^3$ is independently selected from the group consisting of:
$C_{1-6}$ alkyl,
$(CH_2)_nOR^4$,
$(CH_2)_n$-phenyl,
$(CH_2)_n$-naphthyl,
$(CH_2)_n$-heteroaryl,
$(CH_2)_n$-heterocyclyl,
$(CH_2)_nC_{3-7}$ cycloalkyl,
halogen,
$(CH_2)_nN(R^4)_2$,
$(CH_2)_nC\equiv N$,
$(CH_2)_nCO_2R^4$,
$(CH_2)_nCOR^4$,
$NO_2$,
$(CH_2)_nNR^4SO_2R^4$,
$(CH_2)_nSO_2N(R^4)_2$,
$(CH_2)_nS(O)_pR^4$,
$(CH_2)_nNR^4C(O)N(R^4)_2$,
$(CH_2)_nC(O)N(R^4)_2$, $(CH_2)_nC(O)N(OR^4)R^4$,
$(CH_2)_nC(O)N(NH_2)R^4$,
$(CH_2)_nNR^4C(O)R^4$,
$(CH_2)_nNR^4CO_2R^4$,
$O(CH_2)_nC(O)N(R^4)_2$,
$(CH_2)_nP(=O)(OR_4)_2$,
$(CH_2)_nOP(=O)(OR_4)_2$,
$(CH_2)_nO(CH_2)_nP(=O)(OR_4)_2$,
$CF_3$,
$CH_2CF_3$,
$OCF_3$, and
$OCH_2CF_3$;

in which phenyl, naphthyl, heteroaryl, cycloalkyl, and heterocyclyl are optionally substituted with one to three substituents independently selected from halogen, hydroxy, $C_{1-4}$ alkoxy, $C_{3-6}$ cycloalkyl, and $C_{1-4}$ alkyl wherein alkyl is optionally substituted with hydroxy or one to three fluorines; and wherein any methylene ($CH_2$) carbon atom in $R^3$ is optionally substituted with one to two groups independently selected from fluorine, hydroxy, and $C_{1-4}$ alkyl optionally substituted with one to five fluorines; or two substituents when on the same methylene ($CH_2$) group are taken together with the carbon atom to which they are attached to form a cyclopropyl group;

each $R^4$ is independently selected from the group consisting of
hydrogen,
$C_{1-6}$ alkyl,
$(CH_2)_m$-phenyl,
$(CH_2)_m$-heteroaryl,
$(CH_2)_m$-naphthyl, and
$(CH_2)_m C_{3-7}$ cycloalkyl;

wherein alkyl, phenyl, heteroaryl, and cycloalkyl are optionally substituted with one to three groups independently selected from halogen, $C_{1-4}$ alkyl, and $C_{1-4}$ alkoxy, wherein alkyl and alkoxy are optionally substituted with one to five fluorines; or two $R^4$ groups together with the atom to which they are attached form a 4- to 8-membered mono- or bicyclic ring system optionally containing an additional heteroatom selected from O, S, and $NC_{1-4}$ alkyl;

each $R^5$ is independently selected from the group consisting of
$C_{1-6}$ alkyl,
$C_{2-4}$ alkenyl,
$(CH_2)_nOR^4$,
$(CH_2)_n$-phenyl,
$(CH_2)_n$-naphthyl,
$(CH_2)_n$-heteroaryl,
$(CH_2)_n$-heterocyclyl,
$(CH_2)_n C_{3-7}$ cycloalkyl,
halogen,
$(CH_2)_nN(R^4)_2$,
$(CH_2)_nC\equiv N$,
$(CH_2)_nCO_2R^4$,
$(CH_2)_nOC(O)R^4$,
$(CH_2)_nCOR^4$,
$NO_2$,
$(CH_2)_nNR^4SO_2R^4$
$(CH_2)_nSO_2N(R^4)_2$,
$(CH_2)_nS(O)_pR^4$,
$(CH_2)_nNR^4C(O)N(R^4)_2$,
$(CH_2)_nC(O)N(R^4)_2$,
$(CH_2)_nC(O)N(OR^4)R^4$,
$(CH_2)_nC(O)N(NH_2)R^4$,
$(CH_2)_nC(O)NR^4NC(O)R^4$;
$(CH_2)_nNR^4C(O)R^4$,
$(CH_2)_nNR^4CO_2R^4$,
$(CH_2)_nP(=O)(OR_4)_2$,
$(CH_2)_nOP(=O)(OR_4)_2$,
$(CH_2)_nO(CH_2)_nP(=O)(OR_4)_2$,
$O(CH_2)_nC(O)N(R^4)_2$,
$CF_3$,
$CH_2CF_3$,
$OCF_3$, and
$OCH_2CF_3$;

in which phenyl, naphthyl, heteroaryl, cycloalkyl, and heterocyclyl are optionally substituted with one to three substituents independently selected from halogen, hydroxy, $C_{1-4}$ alkoxy, $C_{1-4}$ alkylsulfonyl, $C_{3-6}$ cycloalkyl, and $C_{1-4}$ alkyl wherein alkyl is optionally substituted with carboxy, hydroxy, or one to three fluorines; and wherein any methylene ($CH_2$) carbon atom in $R^5$ is optionally substituted with one to two groups independently selected from fluorine, hydroxy, and $C_{1-4}$ alkyl optionally substituted with one to five fluorines; or two substituents when on the same methylene ($CH_2$) group are taken together with the carbon atom to which they are attached to form a cyclopropyl group;

$R^6$, $R^7$, $R^8$, $R^9$, $R^{10}$, $R^{11}$, and $R^{12}$ are each independently hydrogen or $C_{1-3}$ alkyl, wherein alkyl is optionally substituted with one to three substituents independently selected from fluorine and hydroxyl;

each n is independently 0, 1 or 2;
each m is independently 0, 1, or 2; and
p is 0, 1, or 2.

In one embodiment of the compounds of the present invention, there are provided compounds of structural formula Ia having the indicated absolute stereochemical configuration at the stereogenic azacyclopentane carbon atom marked with an *:

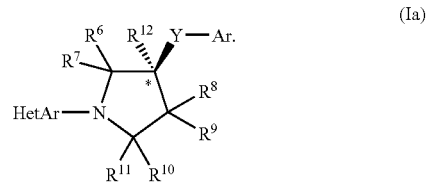

(Ia)

In a class of this embodiment of the compounds of the present invention, Y is O. In a subclass of this class, HetAr is 2-thiazolyl or 1,3,4-thiadiazol-2-yl monosubstituted at the C-5 position of the thiazole or 1,3,4-thiadiazole ring with $R^5$ as defined above. In another subclass of this class, Ar is phenyl or pyridyl optionally substituted with one to three $R^3$ substituents as defined above. In yet another subclass of this class, Ar is phenyl or pyridyl optionally substituted with one to three $R^3$ substituents as defined above, and HetAr is 2-thiazolyl or 1,3,4-thiadiazol-2-yl monosubstituted at the C-5 position of the thiazole or 1,3,4-thiadiazole ring with $R^5$ as defined above.

In a second class of this embodiment of the compounds of the present invention, Y is $S(O)_p$. In a subclass of this class, HetAr is 2-thiazolyl or 1,3,4-thiadiazol-2-yl monosubstituted at the C-5 position of the thiazole or 1,3,4-thiadiazole ring with $R^5$ as defined above. In another subclass of this class, Ar is phenyl or pyridyl optionally substituted with one to three $R^3$ substituents as defined above. In yet another subclass of this class, p is 0, Ar is phenyl or pyridyl optionally substituted with one to three $R^3$ substituents as defined above, and HetAr is 2-thiazolyl or 1,3,4-thiadiazol-2-yl monosubstituted at the C-5 position of the thiazole or 1,3,4-thiadiazole ring with $R^5$ as defined above.

In a third class of this embodiment of the compounds of the present invention, Y is $CR^1R^2$. In a subclass of this class, HetAr is 2-thiazolyl or 1,3,4-thiadiazol-2-yl monosubstituted at the C-5 position of the thiazole or 1,3,4-thiadiazole ring with $R^5$ as defined above. In another subclass of this class, Ar is phenyl or pyridyl optionally substituted with one to three $R^3$ substituents as defined above. In yet another subclass of this class, $R^1$ and $R^2$ are hydrogen, Ar is phenyl or pyridyl optionally substituted with one to three $R^3$ substituents as defined above, and HetAr is 2-thiazolyl or 1,3,4-thiadiazol-2-yl monosubstituted at the C-5 position of the thiazole or 1,3,4-thiadiazole ring with $R^5$ as defined above.

In a second embodiment of the compounds of the present invention, $R^6$, $R^7$, $R^8$, $R^9$, $R^{10}$, $R^{11}$, and $R^{12}$ hydrogen.

In a third embodiment of the compounds of the present invention, each $R^3$ is independently selected from the group consisting of halogen, $C_{1-4}$ alkyl, trifluoromethyl, $C_{1-4}$ alkylsulfonyl, cyano, and $C_{1-4}$ alkoxy.

In a fourth embodiment of the compounds of the present invention, each $R^5$ is independently selected from the group consisting of:
halogen,
cyano,
$C(O)N(R^4)_2$,
$C(O)R^4$,
$CO_2R^4$,
$CH_2OR^4$, wherein $CH_2$ is optionally substituted with one to substituents independently from hydroxy, fluorine, and methyl,
$NR^4C(O)R^4$,
$SO_2N(R^4)_2$, and
heteroaryl which is selected from the group consisting of 1,2,4-oxadiazol-3-yl, 1,2,4-oxadiazol-5-yl, 1,3,4-oxadiazol-2-yl, 2-thiazolyl, and 2H-tetrazol-5-yl, wherein heteroaryl is optionally substituted with one to two substituents independently selected from halogen, hydroxy, $C_{1-4}$ alkoxy, $C_{3-6}$ cycloalkyl, and $C_{1-4}$ alkyl wherein alkyl is optionally substituted with hydroxy or one to three fluorines.

In a fifth embodiment, there are provided compounds of structural formula (Ib) having the indicated absolute stereochemical configuration at the stereogenic azacyclopentane carbon atom marked with an **:

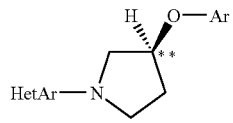
(Ib)

wherein Ar and HetAr are as defined above.

In a class of this embodiment, Ar is phenyl optionally substituted with one to three $R^3$ substituents and HetAr is 2-thiazolyl or 1,3,4-thiadiazol-2-yl monosubstituted at the C-5 position of the thiazole or 1,3,4-thiadiazole ring with $R^5$; each $R^3$ is independently selected from the group consisting of halogen, $C_{1-4}$ alkyl, trifluoromethyl, $C_{1-4}$ alkylsulfonyl, cyano, and $C_{1-4}$ alkoxy; and
each $R^5$ is independently selected from the group consisting of:
halogen,
cyano,
$C(O)N(R^4)_2$,
$C(O)R^4$,
$CO_2R^4$,
$CH_2OR^4$, wherein $CH_2$ is optionally substituted with one to substituents independently from hydroxy, fluorine, and methyl,
$NR^4C(O)R^4$,
$SO_2N(R^4)_2$, and
heteroaryl which is selected from the group consisting of 1,2,4-oxadiazol-3-yl, 1,2,4-oxadiazol-5-yl, 1,3,4-oxadiazol-2-yl, 2-thiazolyl, and 2H-tetrazol-5-yl, wherein heteroaryl is optionally substituted with one to two substituents independently selected from halogen, hydroxy, $C_{1-4}$ alkoxy, $C_{3-6}$ cycloalkyl, and $C_{1-4}$ alkyl wherein alkyl is optionally substituted with hydroxy or one to three fluorines.

In a subclass of this class, $R^5$ is heteroaryl optionally substituted with one to three substituents independently selected from halogen, hydroxy, hydroxymethyl, $C_{1-3}$ alkyl, trifluoromethyl, and $C_{1-3}$ alkoxy. In a subclass of this subclass, heteroaryl is 1,3,4-oxadiazol-2-yl or 1,2,4-oxadiazol-3-yl each of which is optionally substituted with one substituent independently selected from halogen, hydroxy, hydroxymethyl, $C_{1-3}$ alkyl, trifluoromethyl, and $C_{1-3}$ alkoxy.

Illustrative, but nonlimiting examples, of compounds of the present invention that are useful as inhibitors of SCD are the following:

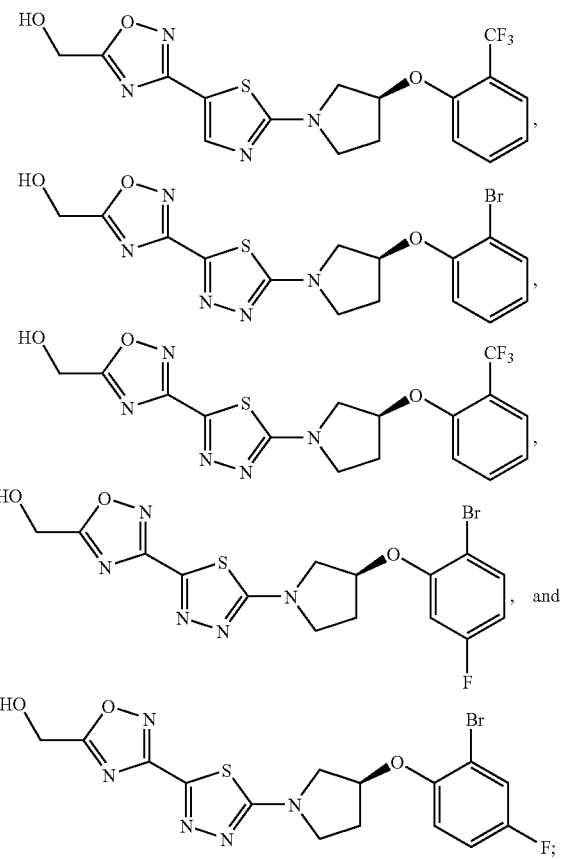

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, 2-oxopiperidin-1-yl, 2-oxopyrrolidin-1-yl, 2-oxoazetidin-1-yl, 1,2,4-oxadiazin-5(6H)-one-3-yl, and the like.

"Heteroaryl" means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylamino ethanol, 2-dimethylamino ethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural formula I are included in the present invention as well.

The subject compounds are useful in a method of inhibiting the stearoyl-coenzyme A delta-9 desaturase enzyme (SCD) in a patient such as a mammal in need of such inhibition comprising the administration of an effective amount of the compound. The compounds of the present invention are therefore useful to control, prevent, and/or treat conditions and diseases mediated by high or abnormal SCD enzyme activity.

Thus, one aspect of the present invention concerns a method of treating hyperglycemia, diabetes or insulin resistance in a mammalian patient in need of such treatment, which comprises administering to said patient an effective amount of a compound in accordance with structural formula I or a pharmaceutically salt or solvate thereof.

A second aspect of the present invention concerns a method of treating non-insulin dependent diabetes mellitus (Type 2 diabetes) in a mammalian patient in need of such treatment comprising administering to the patient an antidiabetic effective amount of a compound in accordance with structural formula I.

A third aspect of the present invention concerns a method of treating obesity in a mammalian patient in need of such treatment comprising administering to said patient a compound in accordance with structural formula I in an amount that is effective to treat obesity.

A fourth aspect of the invention concerns a method of treating metabolic syndrome and its sequelae in a mammalian patient in need of such treatment comprising administering to said patient a compound in accordance with structural formula I in an amount that is effective to treat metabolic syndrome and its sequelae. The sequelae of the metabolic syndrome include hypertension, elevated blood glucose levels, high triglycerides, and low levels of HDL cholesterol.

A fifth aspect of the invention concerns a method of treating a lipid disorder selected from the group consisting of dyslipidemia, hyperlipidemia, hypertriglyceridemia, hypercholesterolemia, low HDL and high LDL in a mammalian patient in need of such treatment comprising administering to said patient a compound in accordance with structural formula I in an amount that is effective to treat said lipid disorder.

A sixth aspect of the invention concerns a method of treating atherosclerosis in a mammalian patient in need of such treatment comprising administering to said patient a compound in accordance with structural formula I in an amount effective to treat atherosclerosis.

A seventh aspect of the invention concerns a method of treating cancer in a mammalian patient in need of such treatment comprising administering to said patient a compound in accordance with structural formula I in an amount effective to treat cancer. In one embodiment of this aspect of the invention, the cancer is liver cancer.

A further aspect of the invention concerns a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) non-alcoholic fatty liver disease or liver steatosis, (21) non-alcoholic steatohepatitis, (22) polycystic ovary syndrome, (23) sleep-disordered breathing, (24) metabolic syndrome, (25) liver fibrosis, (26) cirrhosis of the liver; and (27) other conditions and disorders where insulin resistance is a component, in a mammalian patient in need of such treatment comprising administering to the patient a compound in accordance with structural formula I in an amount that is effective to treat said condition.

Yet a further aspect of the invention concerns a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) non-alcoholic fatty liver disease or liver steatosis, (21) non-alcoholic steatohepatitis, (22) polycystic ovary syndrome, (23) sleep-disordered breathing, (24)

metabolic syndrome, (25) liver fibrosis, (26) cirrhosis of the liver; and (27) other conditions and disorders where insulin resistance is a component, in a mammalian patient in need of such treatment comprising administering to the patient a compound in accordance with structural formula I in an amount that is effective to delay the onset of said condition.

Yet a further aspect of the invention concerns a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) non-alcoholic fatty liver disease or liver steatosis, (21) non-alcoholic steatohepatitis, (22) polycystic ovary syndrome, (23) sleep-disordered breathing, (24) metabolic syndrome, (25) liver fibrosis, (26) cirrhosis of the liver; and (27) other conditions and disorders where insulin resistance is a component, in a mammalian patient in need of such treatment comprising administering to the patient a compound in accordance with structural formula I in an amount that is effective to reduce the risk of developing said condition.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention is further directed to a method for the manufacture of a medicament for inhibiting stearoyl-coenzyme A delta-9 desaturase enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, insulin resistance, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of stearoyl-coenzyme A delta-9 desaturase enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of stearoyl-coenzyme A delta-9 desaturase (SCD) enzyme activity may be demonstrated by the following microsomal and whole-cell based assays:

I. SCD-induced Rat Liver Microsome Assay:

The activity of compounds of formula I against the SCD enzyme is determined by following the conversion of radiolabeled-stearoyl-CoA to oleoyl-CoA using SCD1-induced rat liver microsome and a previously published procedure with some modifications (Joshi, et al., *J. Lipid Res.*, 18: 32-36 (1977)). After feeding wistar rats with a high carbohydrate/fat-free rodent diet (LabDiet # 5803, Purina) for 3 days, the SCD-induced livers were homogenized (1:10 w/v) in 250 mM sucrose, 1 mM EDTA, 5 mM DTT and 50 mM Tris-HCl (pH 7.5). After a 20 min centrifugation (18,000×g/4° C.) to remove tissue and cell debris, the microsome was prepared by a 100,000×g centrifugation (60 min) with the resulting pellet suspended in 100 mM sodium phosphate, 20% glycerol and 2 mM DTT. Test compound in 2 µL DMSO was incubated for 15 min. at room temperature with 180 µL of the microsome (typically at about 100 µg/mL, in Tris-HCl buffer (100 mM, pH 7.5), ATP (5 mM), Coenzyme A (0.1 mM), Triton X-100 (0.5 mM) and NADH (2 mM)). The reaction was initiated by the addition of 20 µL of [$^3$H]-Stearoyl-CoA (final concentration at 2 µM with the radioactivity concentration at 1 µCi/mL), and terminated by the addition of 150 µL of 1N sodium hydroxide. After 60 min at room temperature to hydrolyze the oleoyl-CoA and stearoyl-CoA, the solution was acidified by the addition of 150 µL of 15% phosphoric acid (v/v) in ethanol supplemented with 0.5 mg/mL stearic acid and 0.5 mg/mL oleic acid. [$^3$H]-oleic acid and [$^3$H]-stearic acid were then quantified on a HPLC that is equipped with a C-18 reverse phase column and a Packard Flow Scintillation Analyzer. Alternatively, the reaction mixture (80 µL) was mixed with a calcium chloride/charcoal aqueous suspension (100 µL of 15% (w/v) charcoal plus 20 µL of 2 N $CaCl_2$). The resulting mixture was centrifuged to precipitate the radioactive fatty acid species into a stable pellet. Tritiated water from SCD-catalyzed desaturation of 9,10-[$^3$H]-stearoyl-CoA was quantified by counting 50 µL of the supernant on a scintillation counter.

II. Whole Cell-based SCD (Delta-9), Delta-5 and Delta-6 Desaturase Assays:

Human HepG2 cells were grown on 24-well plates in MEM media (Gibco cat# 11095-072) supplemented with 10% heat-inactivated fetal bovine serum at 37° C. under 5% $CO_2$ in a humidified incubator. Test compound dissolved in the media was incubated with the subconfluent cells for 15 min at 37° C. [1-$^{14}$C]-stearic acid was added to each well to a final concentration of 0.05 µCi/mL to detect SCD-catalyzed [$^{14}$C]-oleic acid formation. 0.05 µCi/mL of [1-$^{14}$C]-eicosatrienoic acid or [1-$^{14}$C]-linolenic acid plus 10 µM of 2-amino-N-(3-chlorophenyl)benzamide (a delta-5 desaturase inhibitor) was used to index the delta-5 and delta-6 desaturase activities, respectively. After 4 h incubation at 37° C., the culture media was removed and the labeled cells were washed with PBS (3×1 mL) at room temperature. The labeled cellular lipids were hydrolyzed under nitrogen at 65° C. for 1 h using 400 μL of 2N sodium hydroxide plus 50 μL of L-α-phosphatidylcholine (2 mg/mL in isopropanol, Sigma #P-3556). After acidification with phosphoric acid (60 μL), the radioactive species were extracted with 300 μL of acetonitrile and quantified on a HPLC that was equipped with a C-18 reverse phase column and a Packard Flow Scintillation Analyzer. The levels of [$^{14}$C]-oleic acid over [$^{14}$C]-stearic acid, [$^{14}$C]-arachidonic acid over [$^{14}$C]-eicosatrienoic acid, and [$^{14}$C]-eicosatetraenoic acid (8,11,14,17) over [$^{14}$C]-linolenic acid were used as the corresponding activity indices of SCD, delta-5 and delta-6 desaturase, respectively.

The SCD inhibitors of formula I, particularly the inhibitors of Examples 1 through 21 exhibit an inhibition constant IC$_{50}$ of less than 1 μM and more typically less than 0.1 μM. Generally, the IC$_{50}$ ratio for delta-5 or delta-6 desaturases to SCD for a compound of formula I, particularly for Examples 1 through 21, is at least about ten or more, and preferably about hundred or more.

In Vivo Efficacy of Compounds of the Present Invention:

The in vivo efficacy of compounds of formula I was determined by following the conversion of [1-$^{14}$C]-stearic acid to [1-$^{14}$C]oleic acid in animals as exemplified below. Mice were dosed with a compound of formula I and one hour later the radioactive tracer, [1-$^{14}$C]-stearic acid, was dosed at 20 μCi/kg IV. At 3 h post dosing of the compound, the liver was harvested and then hydrolyzed in 10 N sodium hydroxide for 24 h at 80° C., to obtain the total liver fatty acid pool. After phosphoric acid acidification of the extract, the amount of [$^{14}$C]-stearic acid and [1-$^{14}$C]-oleic acid was quantified on a HPLC that was equipped with a C-18 reverse phase column and a Packard Flow Scintillation Analyzer.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of formula I, and either administered separately or in the same pharmaceutical composition, include, but are not limited to:

(a) dipeptidyl peptidase IV (DPP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-IB (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide Y$_1$ or Y$_5$ antagonists, CB1 receptor inverse agonists and antagonists, β$_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-IV inhibitor compounds include isoleucine thiazolidide (P32/98); NVP-DPP-728; LAF 237; P93/01; and saxagliptin (BMS 477118).

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. No. 6,294,534, U.S. Pat. Nos. 6,350,760, 6,376,509, 6,410,548, 6,458,790, U.S. Pat. No. 6,472,398, U.S. Pat. No. 5,837,521, U.S. Pat. No. 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02//092566, WO 03/-093234, WO 03/095474, and WO 03/104761.

One particular aspect of combination therapy concerns a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment comprising administering to the patient a therapeutically effective amount of a compound of structural formula I and an HMG-CoA reductase inhibitor.

More particularly, this aspect of combination therapy concerns a method of treating a condition selected from the group consisting of hypercholesterolemia, atherosclerosis, low HDL levels, high LDL levels, hyperlipidemia, hypertriglyceridemia and dyslipidemia in a mammalian patient in need of such treatment wherein the HMG-CoA reductase inhibitor is a statin selected from the group consisting of lovastatin, simvastatin, pravastatin, cerivastatin, fluvastatin, atorvastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound of structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound of structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin selected from the group consisting of: lovastatin, simvastatin, pravastatin, cerivastatin, fluvastatin, atorvastatin, and rosuvastatin.

In another aspect of the invention, a method for delaying the onset or reducing the risk of developing atherosclerosis in a human patient in need of such treatment is disclosed, wherein the HMG-Co A reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises:

(1) a compound of structural formula I;

(2) a compound selected from the group consisting of:

(a) dipeptidyl peptidase IV (DPP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476; and (3) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of stearoyl-CoA delta-9 desaturase enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Preparation of Compounds of the Invention:

The compounds of structural formula I can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESMS).

List of Abbreviations
Alk=alkyl
APCI=atmospheric pressure chemical ionization
Ar=aryl
Boc=tert-butoxycarbonyl
br=broad
Burgess Reagent=3,3,3-triethyl-1-(methoxycarbonyl)diazathian-3-ium-1-ide 2,2-dioxide
Cbz=benzyloxycarbonyl
$CH_2Cl_2$=dichloromethane
$CH_2N_2$=diazomethane
d=doublet
DBU=1,8-diazabicyclo[5.4.0]undec-7-ene
DCC=N,N'-dicyclohexylcarbodiimide
DEAD=diethyl azodicarboxylate
Deoxofluor®=bis(2-methoxyethyl)aminosulfur trifluoride
DIPEA=N,N-diisopropylethylamine
DMF=N,N-dimethylformamide
DMSO=dimethyl sulfoxide
ESI=electrospray ionization
EtOAc=ethyl acetate
HATU=O-(7-azabenzotriazol-1-yl)-N,N,N,N'-tetramethyluronium hexafluorophosphate
HOAc=acetic acid
HOBt=1-hydroxybenzotriazole hydrate
KOH=potassium hydroxide
LiOH=lithium hydroxide
m=multiplet
m-CPBA=3-chloroperoxybenzoic acid
MeOH=methyl alcohol
$MgSO_4$=magnesium sulfate
MS=mass spectroscopy
NaHMDS=sodium bis(trimethylsilyl)amide
NaOH=sodium hydroxide
$Na_2SO_4$=sodium sulfate
$NH_4OAc$=ammonium acetate
NMP=N-methylpyrrolidinone
NMR=nuclear magnetic resonance spectroscopy
PG=protecting group
rt=room temperature
s=singlet
t=triplet
THF=tetrahydrofuran
TFA=trifluoroacetic acid
TFAA=trifluoroacetic anhydride
TLC=thin-layer chromatography
TsCl=p-toluenesulfonyl chloride
p-TsOH=p-toluenesulfonic acid Method A:

An appropriately substituted heteroaryl halide 1 is reacted with an appropriately substituted cyclic amine 2 in the presence of a base such as DBU and an alkali metal (K, Na, Cs) carbonate in a solvent such as THF, 1,4-dioxane, and DMF at a temperature range of about room temperature to about refluxing temperature. Extractive work up and purification by flash column chromatography gives desired product 3.

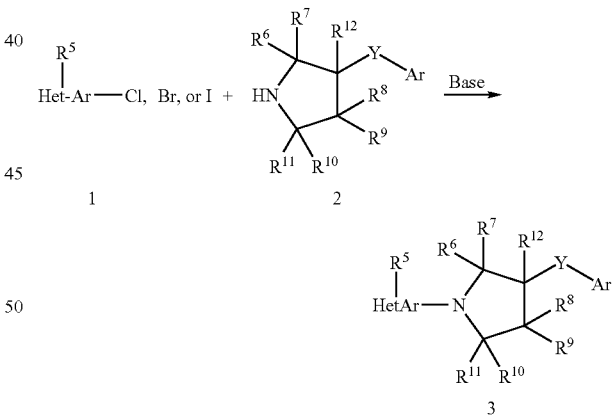

Method B:

An appropriately substituted heteroaryl dibromide 4 is reacted with an appropriately substituted cyclic amine 2 in the presence of a base such as 1,8-diazabicyclo[5.4.0]undec-7-ene (DBU) or an alkali metal (K, Na, Cs) carbonate in a solvent such as N,N-dimethylformamide (DMF) at a temperature range of about room temperature to about refluxing temperature. Extractive work up and purification by flash column chromatography gives desired heteroaryl bromide 5. Reaction of heteroaryl bromide 5 with copper (I) cyanide in a solvent such as DMF, acetonitrile, and 1,4-dioxane at a temperature range of about room temperature to about refluxing temperature followed by extractive work up and purification by flash column chromatography gives desired heteroaryl cyanide 6.

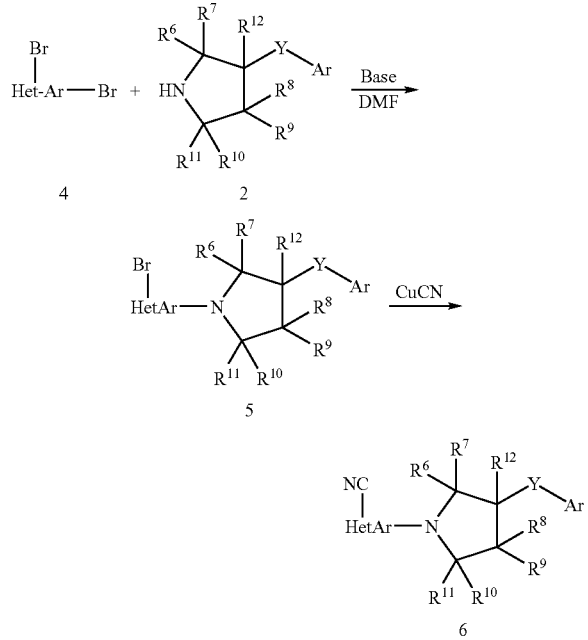

Method C:

The heteroaryl cyanide 6 is converted into amidate 7 by reaction with an appropriate amine in the presence of a base such as DBU and an alkali metal (K, Na, Cs) carbonate in a solvent such as DMF, EtOH, THF, and 1,4-dioxane at a temperature range of about room temperature to about refluxing temperature. Extractive work up and purification by flash column chromatography gives desired amidate 7. The amidate 7 is reacted with an appropriate orthoester in the presence of an acid, such as p-toluenesulfonic acid or $BF_3$-etherate; or an appropriate ester in the presence of a base such as sodium ethoxide to generate the biheteroaryl 8.

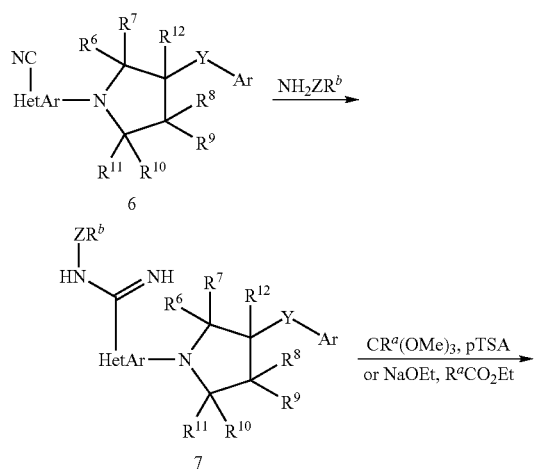

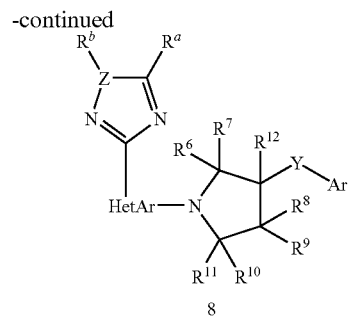

Method D:

An appropriately substituted heteroaryl bromide 9 is reacted with an appropriately substituted cyclic amine 2 in the presence of a base such as DBU or an alkali metal (K, Na, Cs) carbonate in a solvent such as DMF at a temperature range of about room temperature to about refluxing temperature. Extractive work up and purification by flash column chromatography gives desired product 10.

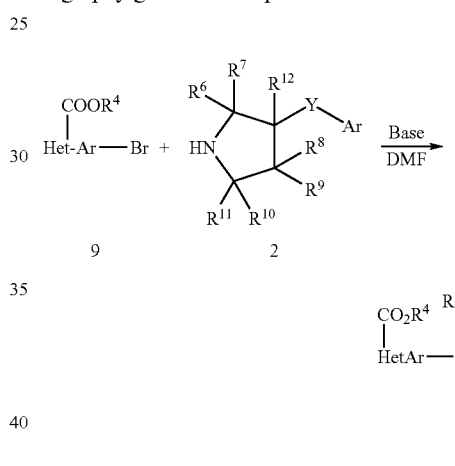

Method E:

The ester 10 is hydrolysed with an alkaline base such as NaOH in a solvent such as aqueous THF with an alcoholic solvent such as MeOH at a temperature range of about room temperature to about refluxing temperature to give the carboxylic acid 11. The carboxylic acid 11 is converted to the corresponding acid chloride and then reacted with an appropriately substituted $R^4R^4NH$ amine to give the desired amide product 12. Alternatively, the carboxylic acid 11 is reacted with an appropriately substituted $R^4R^4NH$ amine in the presence of a standard peptide coupling reagent such as HATU or DCC to give the desired amide product 12.

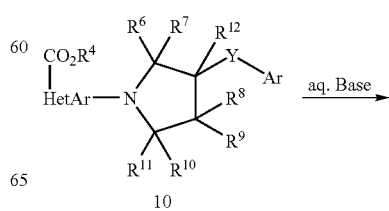

-continued

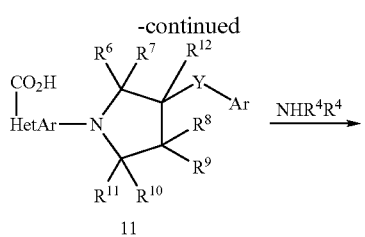
11

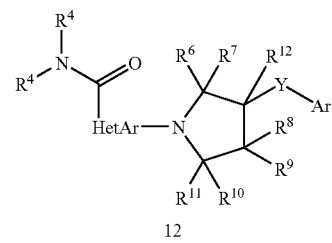
12

Method F:

The carboxylic acid 10 is converted to the corresponding acid chloride and then reacted with an appropriately substituted W—NH$_2$ amine to give the desired amide product 13. Alternatively, the carboxylic acid 13 is reacted with an appropriately substituted W—NH$_2$ amine in the presence of a standard peptide coupling reagent such as HATU or DCC to give the desired amide product 13. The amide 13 can be reacted with an appropriate orthoester in the presence of an acid such as pTSA or BF$_3$-etherate to generate the biheteroaryl 14. Alternatively the amide can be converted to its thioamide by reaction with an appropriate reagent such Lawesson's reagent or P$_4$S$_{10}$. The thioamide in turn can be converted to its corresponding heterocycle.

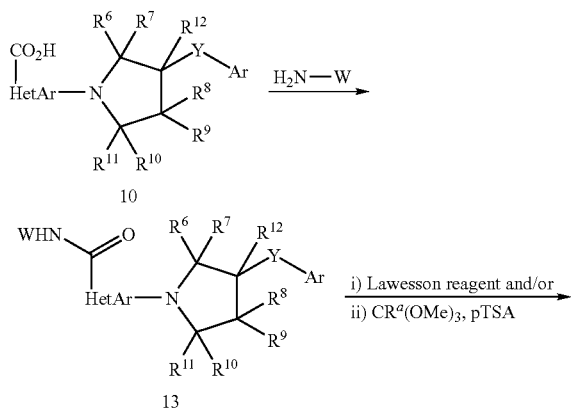

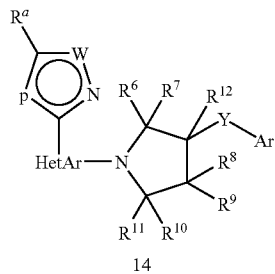
14 p and W are each independently selected from S, O, NR(R=H or alkyl), CH=, and CR=

Method G:

The heteroaryl halide 1 used in Methods A-B can be synthesed from the corresponding heteroarylamines 15. Treatment of 15 with t-butyl nitrite and anhydrous copper(II) halide in a solvent such as CH$_3$CN gives the desired heteroaryl halide 1.

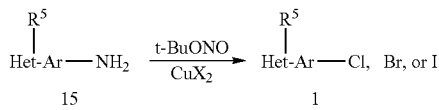

Method H:

A Boc or Cbz protected 4-hydroxypyrrolidine 16 is activated as a mesylate, tosylate or halo (Br or I) derivative via standard conditions. The activated intermediate is then reacted with a ArOH or ArSH nucleophile. Alternatively, intermediate 16 can reacted directly with the nucleophile under Mitsunobu conditions. Deprotection in a standard manner gives the desired amine 2 for the condensation reaction with the heteroaryl halide as shown in Method A.

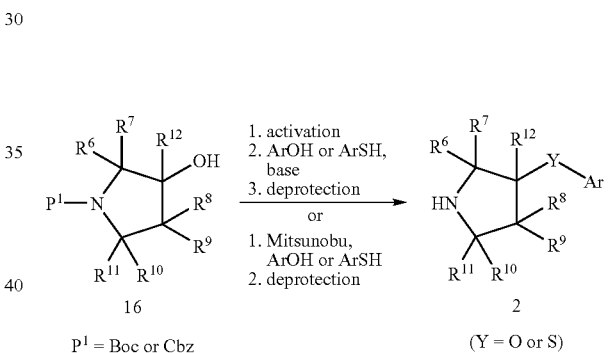

Method I:

A sulfide intermediate 17 from Method H is oxidized with an oxidant, such as meta-chloroperbenzoic acid (mCPBA), NaIO$_4$, and MMPP, in a stoichiometric amount to give either the corresponding sulfoxide (p=1) or sulfone (p=2). Deprotection gives the desired amine 18 for the condensation reaction with the heteroaryl halide as shown in Method A.

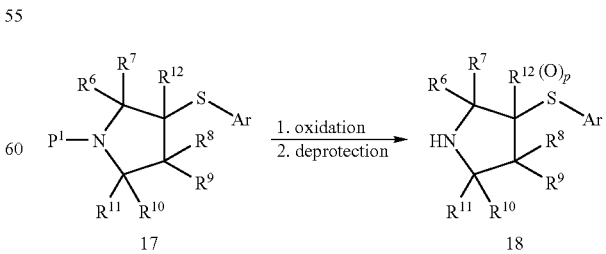

Preparation of Intermediates:

Intermediate 1

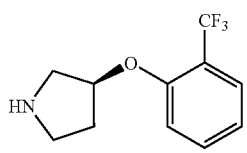

(3S)-3-[2-(Trifluoromethyl)phenoxy]pyrrolidine

To a solution of tert-butyl (3R)-3-hydroxypyrrolidine-1-carboxylate (5 g, 26.7 mmol), 2-(trifluoromethyl)phenol (4.8 h, 29.4 mmol) and triphenylphosphine (8.4 g, 32 mmol) in THF (75 mL) at rt was added DEAD (5.1 mL, 32 mmol) over 5-10 min. The mixture was stirred at rt for 2 days. Solvent was evaporated. The residue was diluted with EtOAc and washed successively with 1 N aqueous NaOH and brine. The EtOAc layer was separated, dried (Na$_2$SO$_4$) and concentrated. Chromatography over silica gel and elution with hexanes/EtOAc (10:1, then 3:1) gave tert-butyl (3R)-3-[2-(trifluoromethyl)phenoxy]pyrrolidine-1-carboxylate as a colorless oil, which solidified on standing. $^1$H NMR (500 MHz, acetone-d$_6$): δ 7.63 (m, 2 H), 7.31 (d, 1 H), 7.13 (t, 1 H), 5.26 (s, 1 H), 3.68-3.43 (m, 4 H), 2.21 (m, 2 H), 1.45 (s, 9 H).

To a solution of tert-butyl (3R)-3-[2-(trifluoromethyl)phenoxy]pyrrolidine-1-carboxylate (8.4 g, 25.4 mmol) in CH$_2$Cl$_2$ (80 mL) at rt was added TFA (8 mL, 4.1 mmol). The mixture was stirred at rt overnight. Solvent was removed in vacuo. The residue was diluted with EtOAc, washed with 1N aqueous NaOH, brine; dried (Na$_2$SO$_4$) and concentrated to give the title compound as a light brown oil. $^1$H NMR (500 MHz, CDCl$_3$): δ 7.58 (d, 1H), 7.49 (t, 1 H), 7.03-6.99 (m, 2 H), 4.97 (t, 1 H), 3.27-3.19 (m, 2 H), 3.02-2.92 (m, 2 H), 2.13-1.99 (m, 2 H).

Intermediate 2

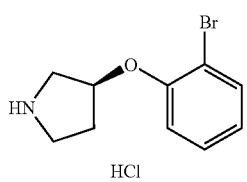

(3S)-3-(2-Bromophenoxy)pyrrolidine hydrochloride

The title compound was prepared in the same manner as described for (3S)-3-[2-(trifluoromethyl)phenoxy]pyrrolidine hydrochloride from tert-butyl (3R)-3-hydroxypyrrolidine-1-carboxylate and 2-bromophenol. $^1$H NMR (300 MHz, DMSO-d$_6$): δ 7.60 (m, 1H), 7.35 (m, 1H), 7.18 (m, 1H), 6.94 (m, 1H), 5.18 (s, 1H), 3.53 (d, 1H), 3.32 (m, 3H), 2.14 (m, 2H).

Intermediate 3

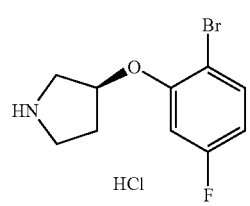

(3S)-3-(2-Bromo-5-fluorophenoxy)pyrrolidine hydrochloride

The title compound was prepared in the same manner as described for (3S)-3-[2-(trifluoromethyl)phenoxy]pyrrolidine hydrochloride from tert-butyl (3R)-3-hydroxypyrrolidine-1-carboxylate and 2-bromo-5-fluorophenol. $^1$H NMR (300 MHz, DMSO-d$_6$): δ 7.62 (m, 1H), 7.19 (m, 1H), 6.84 (m, 1H), 5.22 (s, 1H), 3.53 (s, 1H), 3.32 (m, 3H), 2.14 (m, 2H).

Intermediate 4

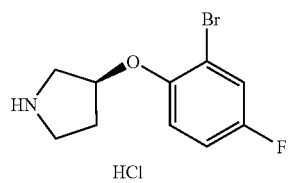

(3S)-3-(2-Bromo-4-fluorophenoxy)pyrrolidine hydrochloride

The title compound was prepared in the same manner as described for (3S)-3-[2-(trifluoromethyl)phenoxy]pyrrolidine hydrochloride from tert-butyl (3R)-3-hydroxypyrrolidine-1-carboxylate and 2-bromo-4-fluorophenol. $^1$H NMR (300 MHz, DMSO-d$_6$): δ 7.62 (m, 1H), 7.32 (m, 1H), 7.13 (m, 1H), 5.31 (s, 1H), 3.60 (m, 1H), 3.32 (m, 3H), 2.12 (m, 2H).

EXAMPLE 1

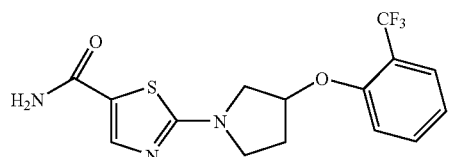

2-{3-[2-(Trifluoromethyl)phenoxy]pyrrolidin-1-yl}-1,3-thiazole-5-carboxamide

Step 1: Methyl 2-(3-hydroxypyrrolidin-1-yl)-1,3-thiazole-5-carboxylate

A mixture of methyl 2-bromo-1,3-thiazole-5-carboxylate (3 g, 13.5 mmol), 3-pyrrolidinol (1.3 g, 14.9 mmol) and DBU (4.1 mL, 27 mmol) in dioxane (50 mL) was heated at 80-85° C. overnight. After cooling, the mixture was diluted with water and extracted five times with EtOAc. The combined EtOAc extracts were washed with water, dried ($Na_2SO_4$) and concentrated to give the crude title compound as a light brown solid. $^1$H NMR (400 MHz, acetone-$d_6$): δ 7.83 (s, 1H), 4.65 (m, 1 H), 4.33 (m, 1 H), 3.79 (s, 3 H), 3.67-3.45 (m, 4 H), 2.29-2.19 (m, 1 H), 2.11 (m, 1 H).

Step 2: Methyl 2-{3-[2-(trifluoromethyl)phenoxy]pyrrolidin-1-yl}-1,3-thiazole-5-carboxylate To a solution of methyl 2-(3-hydroxypyrrolidin-1-yl)-1,3-thiazole-5-carboxylate (1 g, 4.4 mmol), 2-(trifluoromethyl)phenol (0.8 g, 4.9 mmol) and triphenylphosphine (1.5 g, 5.7 mmol) in THF at rt was added DEAD (900 µL, 5.7 mmol) over 5-10 min. The mixture was stirred at rt for 2 days. Solvent was evaporated. The residue was diluted with EtOAc and washed successively with 1 N aqueous NaOH and brine. The EtOAc layer was separated, dried ($Na_2SO_4$) and concentrated. CombiFlash chromatography (40 g, 30-70% EtOAc in hexanes in 20 min, 35 mL/min, 18 mL/fraction) gave a semi-solid which was triturated with hexanes-diethyl ether to give a white solid which was filtered off. Crystals appeared in the mother liquor after standing. These crystals were collected to give the title compound, contaminated with about 5-10% impurity. $^1$H NMR (400 MHz, acetone-$d_6$): δ 7.84 (s, 1 H), 7.67 (m, 2 H), 7.41 (d, 1 H), 7.17 (t, 1H), 5.51 (s, 1H), 3.95 (m, 1H), 3.80-3.65 (m, 6H), 2.60-2.46 (m, 2H).

Step 3: 2-{3-[2-(Trifluoromethyl)phenoxy]pyrrolidin-1-yl}-1,3-thiazole-5-carboxylic acid A mixture of methyl 2-{3-[2-(trifluoromethyl)phenoxy]pyrrolidin-1-yl}-1,3-thiazole-5-carboxylate (1.2 g, 3.2 mmol) and 1M aqueous NaOH (6.4 mL, 6.4 mmol) in THF-MeOH (1:1, 24 mL) was heated at 80° C. bath for 2 h. Volatile solvents were removed in vacuo. The residue was diluted with $H_2O$, acidified with 1M HCl (7 mL) and extracted with EtOAc. The EtOAc extract was washed with $H_2O$, dried ($Na_2SO_4$), concentrated and triturated with $Et_2O$ to give the title compound as white solid. $^1$H NMR (400 MHz, acetone-$d_6$): δ 7.84 (s, 1 H), 7.67 (m, 2 H), 7.41 (d, 1 H), 7.17 (t, 1 H), 5.51 (s, 1 H), 3.95 (m, 1 H), 3.81-3.60 (m, 3 H), 2.60-2.40 (m, 2 H).

Step 4: 2-{3-[2-(Trifluoromethyl)phenoxy]pyrrolidin-1-yl}-1,3-thiazole-5-carboxamide To a solution of 2-{3-[2-(trifluoromethyl)phenoxy]pyrrolidin-1-yl}-1,3-thiazole-5-carboxylic acid (860 mg, 2.4 mmol), HOBt (324 mg, 2.4 mmol), HATU (1.5 g, 3.8 mmol) and $NH_4Cl$ (385 mg, 7.2 mmol) in DMF at rt was added DIPEA (2.1 mL, 12 mmol). The mixture was stirred at rt overnight. After dilution with water, the mixture was extracted twice with EtOAc. The EtOAc extracts were combined, washed twice with 0.5 N NaOH, diluted brine, dried ($Na_2SO_4$) and concentrated. The residue was triturated with $Et_2O$:hexanes (1:1) to give the title compound as a pale yellow solid. $^1$H NMR (500 MHz, acetone-$d_6$): δ 7.79 (s, 1 H), 7.68-7.64 (m, 2 H), 7.39 (d, 1 H), 7.15 (t, 1 H), 5.48 (s, 1 H), 3.91 (m, 1 H), 3.78-3.62 (m, 4 H), 2.57-2.49 (m, 1 H), 2.44-2.40 (m, 1 H). MS (+ESI) m/z 358 (MH$^+$).

EXAMPLE 2

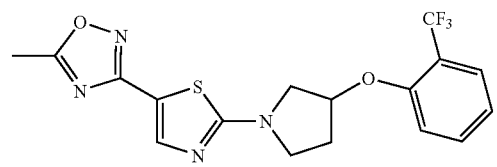

5-Methyl-3-(2-{3-[2-(trifluoromethyl)phenoxy]pyrrolidin-1-yl}-1,3-thiazol-5-yl)-1,2,4-oxadiazole Step 1: 2-{3-[2-(Trifluoromethyl)phenoxy]pyrrolidin-1-yl}-1,3-thiazole-5-carbonitrile A suspension of 2-{3-[2-(trifluoromethyl)phenoxy]pyrrolidin-1-yl}-1,3-thiazole-5-carboxamide (670 mg, 1.9 mmol) and triethylamine (0.92 mL, 6.6 mmol) in $CH_2Cl_2$ (25 mL) was cooled with an ice-acetone bath. Triflic anhydride (412 µL, 2.4 mmol) was added dropwise over 10 min. The mixture was stirred for 5 min and then the cooling bath was removed. After further stirring at rt for 15 min, the mixture was quenched with water and extracted twice with $CH_2Cl_2$. The combined $CH_2Cl_2$ extracts were washed twice with diluted brine, dried ($Na_2SO_4$) and concentrated. Combi-Flash chromatography (40 g, 40-80% EtOAc in hexanes in 20 min, 35 mL/min, 18 mL/fraction) gave a gum that was triturated with hexanes-$Et_2O$ (1:1) to give the title compound as a white powder. $^1$H NMR (400 MHz, acetone-$d_6$): δ 7.88 (s, 1 H), 7.67 (m, 2 H), 7.41 (d, 1 H), 7.18 (t, 1 H), 5.53 (s, 1 H), 3.99 (m, 1 H), 3.85-3.67 (m, 3 H), 2.63-2.45 (m, 2 H). MS (+ESI) m/z 340 (MH$^+$).

Step 2: N'-Hydroxy-2-{3-[2-(trifluoromethyl)phenoxy]pyrrolidin-1-yl}-1,3-thiazole-5-carboximidamide A mixture of 2-{3-[2-(trifluoromethyl)phenoxy]pyrrolidin-1-yl}-1,3-thiazole-5-carbonitrile (370 mg, 1.1 mmol), hydroxylamine hydrochloride (303 mg, 4.4 mmol) and sodium carbonate (231 mg, 2.2 mmol) in EtOH—$H_2O$ (4:1, 20 mL) was heated at 80° C. for 2 h. Solvent was evaporated in vacuo. The residue was diluted with $H_2O$, extracted three times with EtOAc, dried ($Na_2SO_4$) and concentrated. Trituration with hexanes:$Et_2O$ (1:1) gave the title compound as white powder. $^1$H NMR (400 MHz, acetone-$d_6$): δ 8.73 (s, 1 H), 7.66 (m, 2 H), 7.52 (s, 1 H), 7.38 (d, 1 H), 7.16 (t, 1 H), 5.46 (m, 3 H), 3.94-3.88 (m, 1 H), 3.75-3.59 (m, 3 H), 2.56-2.30 (m, 2 H).

Step 3: 5-Methyl-3-(2-{3-[2-(trifluoromethyl)phenoxy]pyrrolidin-1-yl}-1,3-thiazol-5-yl)-1,2,4-oxadiazole To N'-hydroxy-2-{3-[2-(trifluoromethyl)phenoxy]pyrrolidin-1-yl}-1,3-thiazole-5-carboximidamide (190 mg, 0.51 mmol) in pyridine (1.5 mL) at rt was added acetic anhydride (48 µL, 0.51 mmol) and heated at 100° C. for 4 h. After cooling, the reaction mixture was diluted with water, acidified with 1 N HCl (20 mL) and extracted with EtOAc. The EtOAc layer was washed with diluted brine, dried ($Na_2SO_4$) and concentrated. Combi-Flash chromatography (10 g, 50-100% EtOAc in hexanes in 20 min, 20 mL/min, 15 mL/fraction) gave a white solid which was triturated with $Et_2O$ to give the title compound as a white powder. $^1$H NMR (400 MHz, acetone-$d_6$): δ 7.81 (s, 1 H), 7.71-7.65 (m, 2 H), 7.41 (d, 1 H), 7.17 (t, 1 H), 5.52 (s, 1 H), 3.98 (m, 1 H), 3.84-3.67 (m, 3 H), 2.61 (s, 3 H), 2.60-2.43 (m, 2 H). MS (+ESI) m/z 397 (MH⁺).

EXAMPLE 3

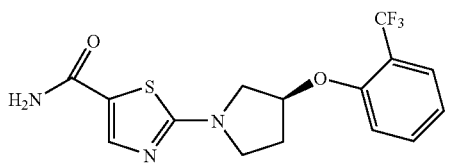

2-{(3S)-3-[2-(Trifluoromethyl)phenoxy]pyrrolidin-1-yl}-1,3-thiazole-5-carboxamide Step 1: Methyl 2-{(3S)-3-[2-(trifluoromethyl)phenoxy]pyrrolidin-1-yl}-1,3-thiazole-5-carboxylate A mixture of methyl 2-bromo-1,3-thiazole-5-carboxylate (2.101 g, 9.46 mmol), (3S)-3-[2-(trifluoromethyl)phenoxy]pyrrolidine (2 g, 8.7 mmol) and DBU (2.7 mL, 17.9 mmol) in dioxane (30 mL) was heated at 80° C. for 24 h. After cooling, the mixture was diluted with water and extracted twice with EtOAc. The combined EtOAc extracts were washed with water, dried and concentrated. Combi-Flash chromatography (120 g, 40-80% EtOAc in hexanes in 20 min, 70 mL/min, 25 mL/fraction) gave the title compound as a white solid. ¹H NMR (400 MHz, acetone-d₆): δ 7.84 (s, 1 H), 7.67 (m, 2 H), 7.41 (d, 1 H), 7.17 (t, 1 H), 5.51 (s, 1 H), 3.95 (m, 1 H), 3.80-3.65 (m, 6 H), 2.60-2.46 (m, 2 H).

Step 2: 2-{(3S)-3-[2-(Trifluoromethyl)phenoxy]pyrrolidin-1-yl}-1,3-thiazole-5-carboxamide The title compound was prepared in the same manner as described for Example 1, Steps 3 and 4 from methyl 2-{(3S)-3-[2-(trifluoromethyl)phenoxy]pyrrolidin-1-yl}-1,3-thiazole-5-carboxylate. ¹H NMR (500 MHz, acetone-d₆): δ 7.79 (s, 1 H), 7.68-7.64 (m, 2 H), 7.39 (d, 1 H), 7.15 (t, 1 H), 5.48 (s, 1 H), 3.91 (m, 1 H), 3.78-3.62 (m, 4 H), 2.57-2.49 (m, 1 H), 2.44-2.40 (m, 1 H). MS (+ESI) m/z 358 (MH⁺).

EXAMPLE 4

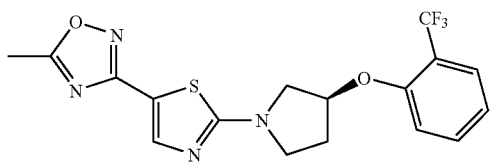

5-Methyl-3-(2-{(3S)-3-[2-(trifluoromethyl)phenoxy]pyrrolidin-1-yl}-1,3-thiazol-5-yl)-1,2,4-oxadiazole Step 1: N'-Hydroxy-2-{(3S)-3-[2-(trifluoromethyl)phenoxy]pyrrolidin-1-yl}-1,3-thiazole-5-carboximidamide The title compound was prepared in the same manner as described for Example 2, Steps 1 and 2 from 2-{(3S)-3-[2-(trifluoromethyl)phenoxy]pyrrolidin-1-yl}-1,3-thiazole-5-carboxamide. ¹H NMR (400 MHz, acetone-d₆): δ 8.73 (s, 1 H), 7.66 (m, 2 H), 7.52 (s, 1 H), 7.38 (d, 1 H), 7.16 (t, 1 H), 5.46 (m, 3 H), 3.94-3.88 (m, 1 H), 3.75-3.59 (m, 3 H), 2.56-2.30 (m, 2 H).

Step 2: 5-Methyl-3-(2-{(3S)-3-[2-(trifluoromethyl)phenoxy]pyrrolidin-1-yl}-1,3-thiazol-5-yl)-1,2,4-oxadiazole To a suspension of N'-hydroxy-2-{(3S)-3-[2-(trifluoromethyl)phenoxy]-pyrrolidin-1-yl}-1,3-thiazole-5-carboximidamide (410 mg, 1.1 mmol) in EtOH (3 mL) and EtOAc (5 mL) was added NaOEt (1.7 mL, 4.4 mmol, 25 wt. %) at rt. The mixture was heated at 80° C. for 30 min. After cooling to rt, the mixture was diluted with water and extracted with EtOAc. The EtOAc extract was washed with water, dried (Na₂SO₄) and concentrated. Combi-Flash chromatography (10 g, 50-100% EtOAc in hexanes in 20 min, 35 mL/min, 15 mL/fraction) gave the title compound after trituration with Et₂O-hexanes (1:1). ¹H NMR (400 MHz, acetone-d₆): δ 7.81 (s, 1 H), 7.71-7.65 (m, 2 H), 7.41 (d, 1 H), 7.17 (t, 1 H), 5.52 (s, 1 H), 3.98 (m, 1 H), 3.84-3.67 (m, 3 H), 2.61 (s, 3H), 2.60-2.43 (m, 2 H). MS (+ESI) m/z 397 (MH⁺).

EXAMPLE 5

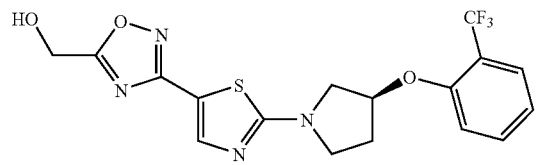

[3-(2-{(3S)-3-[2-(Trifluoromethyl)phenoxy]pyrrolidin-1-yl}-1,3-thiazol-5-yl)-1,2,4-oxadiazol-5-yl]methanol A mixture of N'-hydroxy-2-{(3S)-3-[2-(trifluoromethyl)phenoxy]-pyrrolidin-1-yl}-1,3-thiazole-5-carboximidamide (373 mg, 1 mmol), ethyl glycolate (380 µL, 4 mmol) and sodium ethoxide, (21 wt. % solution in ethyl alcohol, 1.6 mL, 4.2 mmol) in ethanol (10 mL) was refluxed for 30 min. After cooling to rt, the mixture was diluted with water and extracted with EtOAc. The EtOAc extract was washed with water, dried (Na₂SO₄) and concentrated. The residue was triturated with Et₂O to give the title compound as a pale yellow powder. ¹H NMR (500 MHz, acetone-d₆): δ 7.83 (s, 1 H), 7.69-7.65 (m, 2 H), 7.41 (d, 1 H), 7.16 (t, 1 H), 5.52 (m, 1 H), 5.05 (s, 1 H), 4.87 (s, 2 H), 3.98 (m, 1 H), 3.85-3.69 (m, 3 H), 2.60-2.44 (m, 2 H).

MS (+ESI) m/z 413 (MH⁺).

EXAMPLE 6

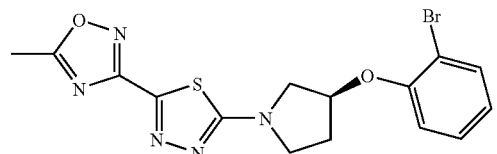

3-{5-[(3S)-3-(2-Bromophenoxy)pyrrolidin-1-yl]-1,3,4-thiadiazol-2-yl}-5-methyl-1,2,4-oxadiazole Step 1: 5-Bromo-1,3,4-thiadiazole-2-carbonitrile To a suspension of 5-bromo-1,3,4-thiadiazol-2-amine (10 g, 0.055 mol) and cuprous cyanide (10.5 g, 0.119 mol) in acetonitrile (200 mL) at 0° C. was added dropwise t-BuONO (12 g, 0.116 mol) over 20 min. The suspension was stirred at room temperature until TLC showed that the reaction was completed. The reaction mixture was then filtered and the filtrate was concentrated in vacuo to give the crude product which was purified by chromatography to give the title product.

$^{13}$C NMR (300 MHz, CDCl$_3$): δ 77.3, 109.0, 141.7.

Step 2: 5-[(3S)-3-(2-Bromophenoxy)pyrrolidin-1-yl]-1,3,4-thiadiazole-2-carbonitrile To a mixture of 4-(2-bromophenoxy)pyrrolidine hydrochloride (0.5 g, 1.87 mmol) and 5-bromo-1,3,4-thiadiazole-2-carbonitrile (0.36 g, 1.87 mmol) in DMF (10 mL) was added K$_2$CO$_3$ (0.77 g, 5.61 mmol) under a nitrogen atmosphere. The mixture was stirred at 70° C. for 4 h. After dilution with water, the mixture was extracted with ethyl acetate. The combined organic extracts were washed with brine, dried over anhydrous Na$_2$SO$_4$, filtered and purified by preparative TLC with petroleum:EtOAc (2:1) to give the title compound. $^1$H NMR (300 MHz, CDCl$_3$): δ 7.58 (d, 1H), 7.52 (t, 1H), 7.08 (t, 1H), 6.99 (d, 1H), 5.24 (m, 1H), 3.69-3.93 (m, 4H), 2.33-2.56 (m, 2H).

Step 3: 3-{5-[(3S)-3-(2-Bromophenoxy)pyrrolidin-1-yl]-1,3,4-thiadiazol-2-yl}-5-methyl-1,2,4-oxadiazole The title compound was prepared in the same manner as described for Steps 2 and 3 of Example 2 from 5-[(3S)-3-(2-bromophenoxy)pyrrolidin-1-yl]-1,3,4-thiadiazole-2-carbonitrile. $^1$H NMR (300 MHz, CDCl$_3$): δ 7.55 (d, 1H), 7.29 (m 1H), 6.91 (m, 2H), 5.13 (m, 1H), 3.70-3.98 (m, 4H), 2.68 (s, 3H), 2.35-2.55 (m, 2H). MS: m/z 408, 410 (MH$^+$).

EXAMPLE 7

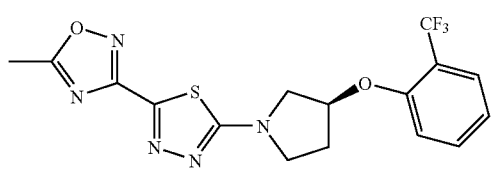

5-Methyl-3-(5-{(3S)-3-[2-(trifluoromethyl)phenoxy]pyrrolidin-1-yl}-1,3,4-thiadiazol-2-yl)-1,2,4-oxadiazole The title compound was prepared in the same manner as described for Steps 2 and 3 of Example 6 from (3S)-3-[2-(trifluoromethyl)phenoxy]pyrrolidine hydrochloride and 5-bromo-1,3,4-thiadiazole-2-carbonitrile. $^1$H NMR (300 MHz, CDCl$_3$): δ 7.58 (d, 1H), 7.51 (t, 1H), 7.07 (t, 1H), 6.99 (t, 1H), 5.22 (m, 1H), 3.97 (s, 2H), 3.71-3.88 (m, 2H), 2.67 (s, 3H), 2.37-2.54 (m, 2H). MS: m/z 398 (MH$^+$).

EXAMPLE 8

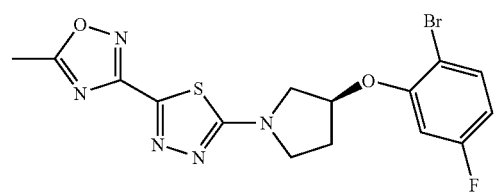

3-{5-[(3S)-3-(2-Bromo-5-fluorophenoxy)pyrrolidin-1-yl]-1,3,4-thiadiazol-2-yl}-5-methyl-1,2,4-oxadiazole The title compound was prepared in the same manner as described for Steps 2 and 3 of Example 6 from (3S)-3-(2-bromo-5-fluorophenoxy)pyrrolidine hydrochloride and 5-bromo-1,3,4-thiadiazole-2-carbonitrile. $^1$H NMR (300 MHz, CDCl$_3$): δ 7.49 (m, 1H), 6.65 (m, 2H), 5.11 (m, 1H), 3.80-3.96 (m, 4H), 2.68 (s, 3H), 2.30-2.55 (m, 2H). MS: m/z 426, 428 (MH$^+$).

EXAMPLE 9

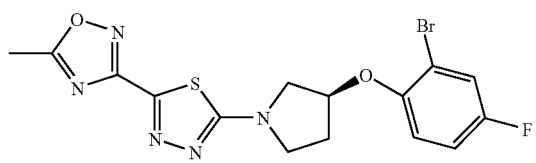

3-{5-[(3S)-3-(2-Bromo-4-fluorophenoxy)pyrrolidin-1-yl]-1,3,4-thiadiazol-2-yl}-5-methyl-1,2,4-oxadiazole The title compound was prepared in the same manner as described for Steps 2 and 3 of Example 6 from (3S)-3-(2-bromo-4-fluorophenoxy]pyrrolidine hydrochloride and 5-bromo-1,3,4-thiadiazole-2-carbonitrile. $^1$H NMR (300 MHz, CDCl$_3$): δ 7.30 (m, 1H), 7.00 (m, 1H), 6.90 (m, 1H), 5.06 (m, 1H), 3.70-3.96 (m, 4H), 2.68 (s, 3H), 2.30-2.55 (m, 2H). MS: m/z 426, 428 (MH$^+$).

EXAMPLE 10

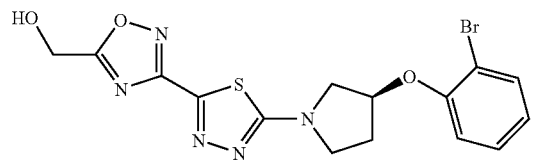

(3-{5-[(3S)-3-(2-Bromophenoxy)pyrrolidin-1-yl]-1,3,4-thiadiazol-2-yl}-1,2,4-oxadiazol-5-yl)methanol The title compound was prepared according to the procedure described for Example 6, step 2; Example 2, step 2; and Example 5 from (3S)-3-(2-bromophenoxy)pyrrolidine hydrochloride and 5-bromo-1,3,4-thiadiazole-2-carbonitrile. $^1$H NMR (400 MHz, CDCl$_3$): δ 7.55 (d, 1H), 7.30 (m, 1H), 6.92 (m, 2H), 5.14 (m, 1H), 5.00 (s, 2H), 3.95 (m, 3H), 3.78 (m, 1H), 2.30-2.54 (m, 2H). MS: m/z 424, 426 (MH$^+$).

EXAMPLE 11

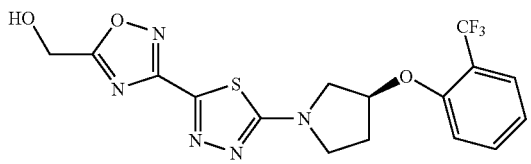

[3-(5-{(3S)-3-[2-(Trifluoromethyl)phenoxy]pyrrolidin-1-yl}-1,3,4-thiadiazol-2-yl)-1,2,4-oxadiazol-5-yl]methanol The title compound was prepared according to the procedure described for Example 6, step 2; Example 2, step 2; and Example 5 from (3S)-3-[2-(trifluoromethyl)phenoxy]-pyrrolidine hydrochloride and 5-bromo-1,3,4-thiadiazole-2-carbonitrile. $^1$H NMR (400 MHz, CDCl$_3$): δ 7.58 (d, 1H), 7.51 (t, 1H), 7.07 (t, 1H), 7.00 (d, 1H), 5.23 (m, 1H), 5.00 (s, 2H), 3.96 (m, 2H), 3.70-3.90 (m, 2H), 2.30-2.54 (m, 2H). MS: m/z 414 (MH$^+$).

EXAMPLE 12

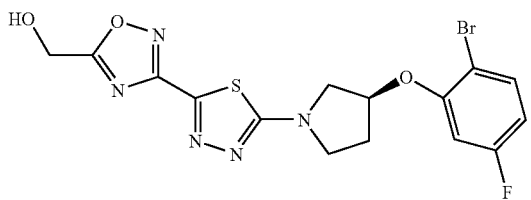

(3-{5-[(3S)-3-(2-Bromo-5-fluorophenoxy)pyrrolidin-1-yl]-1,3,4-thiadiazol-2-yl}-1,2,4-oxadiazol-5-yl)methanol The title compound was prepared according to the procedure described for Example 6, step 2; Example 2, step 2; and Example 5 from (3S)-3-(2-bromo-5-fluorophenoxy)pyrrolidine hydrochloride and 5-bromo-1,3,4-thiadiazole-2-carbonitrile. $^1$H NMR (400 MHz, CDCl$_3$): δ 7.49 (m, 1H), 6.66 (m, 2H), 5.10 (m, 1H), 5.00 (s, 2H), 3.70-4.00 (m, 4H), 2.30-2.54 (m, 2H). MS: m/z 442, 444 (MH$^+$).

EXAMPLE 13

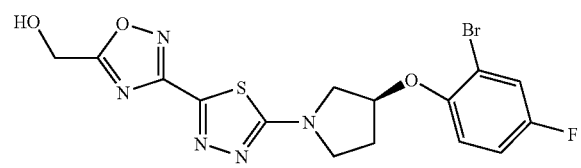

(3-{5-[(3S)-3-(2-Bromo-5-fluorophenoxy)pyrrolidin-1-yl]-1,3,4-thiadiazol-2-yl}-1,2,4-oxadiazol-5-yl)methanol The title compound was prepared according to the procedure described for Example 6, step 2; Example 2, step 2; and Example 5 from (3S)-3-(2-bromo-4-fluorophenoxy)pyrrolidine hydrochloride and 5-bromo-1,3,4-thiadiazole-2-carbonitrile. $^1$H NMR (400 MHz, CDCl$_3$): δ 7.31 (m, 1H), 7.02 (m, 1H), 6.90 (m, 1H), 5.10 (m, 1H), 5.00 (s, 2H), 3.70-4.00 (m, 4H), 2.30-2.54 (m, 2H). MS: m/z 442, 444 (MH$^+$).

EXAMPLE 14

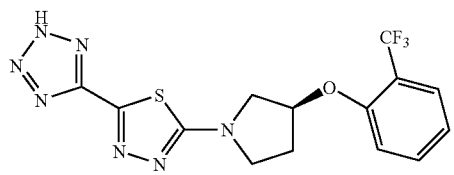

5-(5-{(3S)-3-[2-(Trifluoromethyl)phenoxy]pyrrolidin-1-yl}-1,3,4-thiadiazol-2-yl)-2H-tetrazole Step 1: 5-{(3S)-3-[2-(Trifluoromethyl)phenoxy]pyrrolidin-1-yl}-1,3,4-thiadiazole-2-carbonitrile The title compound was prepared according to the procedure described for Example 6, step 2 from (3S)-3-[2-(trifluoromethyl)phenoxy]-pyrrolidine hydrochloride and 5-bromo-1,3,4-thiadiazole-2-carbonitrile.

Step 2: 5-{(3S)-3-[2-(Trifluoromethyl)phenoxy]pyrrolidin-1-yl}-1,3,4-thiadiazole-2-carbonitrile To a suspension of 5-{(3S)-3-[2-(trifluoromethyl)phenoxy]pyrrolidin-1-yl}-1,3,4-thiadiazole-2-carbonitrile (0.4 g, 1.176 mmol) and ZnBr$_2$ (0.261 g, 1.176 mmol) in i-PrOH (4 mL) and H$_2$O (2 mL) was added NaN$_3$ (0.154 g, 2.35 mmol) in a sealed tube. The mixture was stirred at 120° C. overnight and cooled to RT and then adjusted pH to 4 with HCl (2 M). The reaction mixture was extracted with DCM and the combined organic layers were dried over Na$_2$SO$_4$, filtered and concentrated in vacuum to give the crude product, which was purified by preparative TLC to afford the title compound.

¹H NMR (400 MHz, CDCl₃): δ 7.57 (d, 1H), 7.51 (t, 1H), 7.06 (t, 1H), 7.00 (d, 1H), 5.26 (s, 1H), 3.70-4.13 (m, 4H), 2.27-2.54 (m, 2H). MS m/z 384 (MH⁺).

EXAMPLE 15

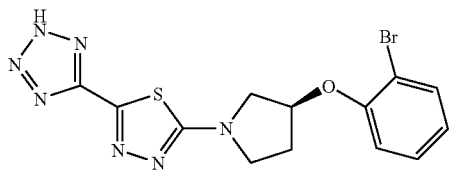

5-{5-[(3S)-3-(2-Bromophenoxy)pyrrolidin-1-yl]-1,3,4-thiadiazol-2-yl}-2H-tetrazole The title compound was prepared according to the procedure described for Example 14 from (3S)-3-(2-bromophenoxy)pyrrolidine hydrochloride and 5-bromo-1,3,4-thiadiazole-2-carbonitrile.

¹H NMR (400 MHz, acetone-d₆): δ 7.62 (d, 1H), 7.42 (t, 1H), 7.30 (d, 1H), 7.00 (t, 1H), 5.42 (m, 1H), 4.05 (dd, 1H), 3.88 (m, 3H), 2.52 (m, 2H). MS (+ESI) m/z 394, 396 (MH⁺).

EXAMPLE 16

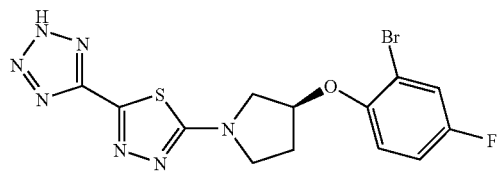

5-{5-[(3S)-3-(2-bromo-4-fluorophenoxy)pyrrolidin-1-yl]-1,3,4-thiadiazol-2-yl}-2H-tetrazole The title compound was prepared according to the procedure described for Example 14 from (3S)-3-(2-bromo-4-fluorophenoxy)pyrrolidine hydrochloride and 5-bromo-1,3,4-thiadiazole-2-carbonitrile.

¹H NMR (400 MHz, acetone-d₆): δ 7.48 (dd, 1H), 7.32 (m, 1H), 7.22 (m, 1H), 5.40 (m, 1H), 4.05 (dd, 1H), 3.88 (m, 3H), 2.52 (m, 2H). MS (+ESI) m/z 412, 414 (MH⁺).

EXAMPLE 17

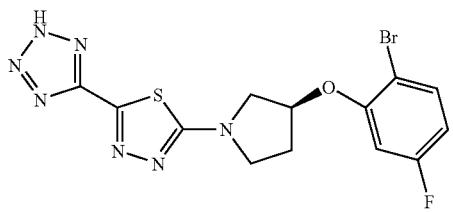

5-{5-[(3S)-3-(2-bromo-5-fluorophenoxy)pyrrolidin-1-yl]-1,3,4-thiadiazol-2-yl}-2H-tetrazole The title compound was prepared according to the procedure described for Example 14 from (3S)-3-(2-bromo-5-fluorophenoxy)pyrrolidine hydrochloride and 5-bromo-1,3,4-thiadiazole-2-carbonitrile.

¹H NMR (400 MHz, acetone-d₆): δ 7.62 (dd, 1H), 7.18 (dd, 1H), 6.82 (m, 1H), 5.48 (m, 1H), 4.00 (dd, 1H), 3.90 (m, 3H), 2.55 (m, 2H). MS (+ESI) m/z 412, 414 (MH⁺).

EXAMPLE 18

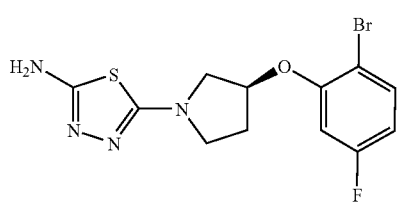

5-[(S)-3-(2-Bromo-5-fluoro-phenoxy)-pyrrolidin-1-yl-][1,3,4]thiadiazol-2-ylamine Step 1: 5-Bromo-1,3,4-thiadiazol-2-amine To a mixture of 1,3,4-thiadiazol-2-amine (38 g, 375 mmol) and sodium acetate (102 g, 750 mmol) in acetic acid (375 mL) was added bromine (20.2 mL, 394 mmol) dropwise at room temperature. The orange mixture was stirred at room temperature for a further 2 h then diluted with saturated sodium bisulfite solution until the orange color disappeared. The mixture was diluted with water (300 mL), stirred for 0.5 h then filtered and washed with water. The solid was dried under high vacuum to give the desired product as a white solid. ¹H NMR (500 MHz, DMSO-d₆): δ 7.55 (s, 2H)

Step 2: 5-[(S)-3-(2-Bromo-5-fluoro-phenoxy)-pyrrolidin-1-yl]-[1,3,4]thiadiazol-2-ylamine A mixture of 5-bromo-1,3,4-thiadiazol-2-amine (1 g, 5.6 mmol), (3S)-3-(2-bromo-5-fluorophenoxy)pyrrolidine (1.6 g, 6.1 mmol) and sodium carbonate (1.2 g, 11 mmol) in EtOH (11 mL) was degassed with nitrogen for 5 mins. The mixture was then heated at 90° C. for 3 h. The mixture was then cooled to room temperature and filtered. The solvent was evaporated and diluted with water (50 mL). The solid precipitate was filtered and washed with water followed by Et₂O to afford the title product.

¹H NMR (500 MHz, acetone-d₆): δ 7.63 (dd, 1H), 7.09 (d, 1H), 6.78 (td, 1H), 5.72 (br s, 2H), 5.32-5.30 (m, 1H), 3.82 (dd, 1H), 3.71-3.51 (m, 3H), 2.51-2.42 (m, 1H), 2.35-2.28 (m, 1H). MS: m/z 359, 361 (MH⁺).

EXAMPLE 19

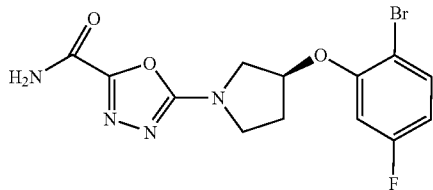

5-[(S)-3-(2-Bromo-5-fluoro-phenoxy)-pyrrolidin-1-yl]-[1,3,4]oxadiazole-2-carboxamide Step 1: Ethyl 5-bromo-1,3,4-oxadiazole-2-carboxylate To a suspension of ethyl 5-amino-1,3,4-oxadiazole-2-carboxylate (8.8 g, 56 mmol) in $CH_3CN$ (187 mL) was added $CuBr_2$ (18.8 g, 84 mmol). The mixture turned dark green and further stirred for 15 min at room temperature. t-BuONO, 90% (15 mL, 112 mmol) was added and stirred at room temperature for 2 h then heated at 50° C. for 0.5 h. The solvent was then evaporated in vacuo. Water (100 mL) and EtOAc (100 mL) were added and the mixture was filtered through celite and washed with EtOAc. The EtOAc layer was separated, and the aqueous layer extracted with EtOAc (2×50 mL). The combined organic layers were dried over $Na_2SO_4$ and concentrated. The product was recrystallized from $CH_2Cl_2$/hexanes to give the title compound as solid. $^1H$ NMR (400 MHz, $CDCl_3$): δ 4.56 (q, 2H), 1.51 (t, 3H).

Step 2: Ethyl-5-[(3S)-3-(2-bromo-5-fluorophenoxy)pyrrolidin-1-yl]-1,3,4-oxadiazole-2-carboxylate To a mixture of ethyl 5-bromo-1,3,4-oxadiazole-2-carboxylate (0.5 g, 2.26 mmol) and (3S)-3-(2-bromo-5-fluorophenoxy)pyrrolidine (0.5 mL, 3.4 mmol) in THF (4.5 mL) was added DBU (0.5 mL, 3.4 mmol). The mixture was stirred at room temperature for 0.5 h then filtered and the filtrate concentrated. Purification by Combiflash ($SiO_2$, gradient elution 70-100% EtOAc/Hexanes) afforded the desired product as solid.

$^1H$ NMR (500 MHz, acetone-$d_6$): δ 7.62 (dd, 1H), 7.15 (d, 1H), 6.79 (td, 1H), 5.46-5.40 (m, 1H), 4.43 (q, 2H), 4.08 (dd, 1H), 3.92-3.80 (m, 3H), 2.52-2.40 (m, 2H), 1.38 (t, 3H). MS: m/z 400, 402 ($MH^+$).

Step 3: 5-[(S)-3-(2-Bromo-5-fluoro-phenoxy)-pyrrolidin-1-yl]-[1,3,4]oxadiazole-2-carboxamide A mixture of ethyl-5-[(3S)-3-(2-bromo-5-fluorophenoxy)pyrrolidin-1-yl]-1,3,4-oxadiazole-2-carboxylate (480 mg, 1.2 mmol) in THF (4 mL) was saturated with ammonia gas for 2 min. The mixture was stirred at room temperature for 0.5 h. The solvent was evaporated and the crude product was dissolved in $Et_2O$, filtered and washed with $Et_2O$ to afford the title product as a solid.

$^1H$ NMR (500 MHz, acetone-$d_6$): δ 7.63 (dd, 1H), 7.55 (br s, 1H), 7.15 (d, 1H), 7.05 (br s, 1H), 6.79 (td, 1H), 5.42-5.38 (m, 1H), 3.98 (dd, 1H), 3.90-3.78 (m, 3H), 2.55-2.38 (m, 2H). MS: m/z 371, 373 ($MH^+$).

EXAMPLE 21

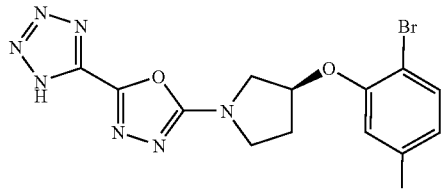

5-{5-[(S)-3-(2-Bromo-5-fluoro-phenoxy)-pyrrolidin-1-yl]-[1,3,4]oxadiazol-2-yl}-1H-tetrazole Step 1: 5-{5-[(S)-3-(2-Bromo-5-fluoro-phenoxy)-pyrrolidin-1-yl]-[1,3,4]oxadiazol-2-Yl}-carbonitrile To a solution of 5-[(S)-3-(2-bromo-5-fluoro-phenoxy)-pyrrolidin-1-yl]-[1,3,4]oxadiazole-2-carboxamide (380 mg, 1 mmol) and $Et_3N$ (0.33 mL, 2.4 mmol) in THF (2 mL) at 0° C. was added TFAA (0.15 mL, 1.1 mmol). After 0.5 h, the mixture was warmed to room temperature and stirred for 0.5 h. The solvent was evaporated in vacuo. The residue was diluted with water (2 mL) and extracted with EtOAc (3×2 mL). The combined organic layers were dried over $Na_2SO_4$ and concentrated to give the title compound which was used crude over the next step.

$^1H$ NMR (500 MHz, acetone-$d_6$): δ 7.63 (dd, 1H), 7.15 (d, 1H), 6.79 (td, 1H), 5.42-5.48 (m, 1H), 4.06 (dd, 1H), 3.96-3.82 (m, 3H), 2.58-2.42 (m, 2H). MS: m/z 353, 355 ($MH^+$).

Step 2: 5-{5-[(S)-3-(2-Bromo-5-fluoro-phenoxy)-pyrrolidin-1-yl]-[1,3,4]oxadiazol-2-yl}-1H-tetrazole A mixture of 5-{5-[(S)-3-(2-Bromo-5-fluoro-phenoxy)-pyrrolidin-1-yl]-[1,3,4]oxadiazol-2-yl}-carbonitrile (150 mg, 0.44 mmol), $NaN_3$ (58 mg, 0.89 mmol) and ammonium chloride (2.2 mmol) in DMF (1.5 mL) was heated at 130° C. for 1 h. The reaction mixture was cooled to room temperature and diluted with aqueous 2N NaOH (1 mL) and washed with EtOAc (2 mL). The aqueous layer was acidified with 6N HCl (2 mL) and extracted with EtOAc (3×2 mL). The combined organic layers were washed with water (2 mL) and dried over $Na_2SO_4$. The solvent was evaporated and triturated with $Et_2O$ to afford the title product.

$^1H$ NMR (500 MHz, acetone-$d_6$): δ 7.98 (s, 1H), 7.63-7.54 (m, 1H), 7.08 (d, 1H), 6.82-6.73 (m, 1H), 5.45-5.42 (m, 1H), 4.12-3.85 (m, 4H), 2.58-2.32 (m, 2H). MS: m/z 396, 398 ($MH^+$).

Example of a Pharmaceutical Formulation

As a specific embodiment of an oral composition of a compound of the present invention, 50 mg of the compound of any of the Examples is formulated with sufficient finely divided lactose to provide a total amount of 580 to 590 mg to fill a size 0 hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of structural formula I:

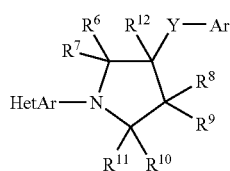

(I)

or a pharmaceutically acceptable salt thereof; wherein
Y is O, S(O)p, or $CR^1R^2$;
Ar is phenyl, benzyl, naphthyl, or pyridyl each of which is optionally substituted with one to five substituents independently selected from $R^3$;
HetAr is an heteroaromatic ring selected from the group consisting of:
thiazolyl and
1,3,4-thiadiazolyl;
in which the heteroaromatic ring is optionally substituted with one to two substituents independently selected from $R^5$;
$R^1$ and $R^2$ are each independently hydrogen or $C_{1-3}$ alkyl, wherein alkyl is optionally substituted with one to three substituents independently selected from fluorine and hydroxy;
each $R^3$ is independently selected from the group consisting of:
$C_{1-6}$ alkyl,
$(CH_2)_nOR^4$,
$(CH_2)_n$-phenyl,
$(CH_2)_n$-naphthyl,
$(CH_2)_n$-heteroaryl,
$(CH_2)_nC_{3-7}$ cycloalkyl, halogen,
$(CH_2)_nN(R^4)_2$,
$(CH_2)_nC{\equiv}N$,
$(CH_2)_nCO_2R^4$,
$(CH_2)_nCOR^4$,
$NO_2$,
$(CH_2)_nNR^4SO_2R^4$
$(CH_2)_nSO_2N(R^4)_2$,
$(CH_2)_nS(O)_pR^4$,
$(CH_2)_nNR^4C(O)N(R^4)_2$,
$(CH_2)_nC(O)N(R^4)_2$,
$(CH_2)_nC(O)N(OR^4)R^4$,
$(CH_2)_nC(O)N(NH_2)R^4$,
$(CH_2)_nNR^4C(O)R^4$,
$(CH_2)_nNR^4CO_2R^4$,
$O(CH_2)_nC(O)N(R^4)_2$,
$(CH_2)_nP(=O)(OR_4)_2$,
$(CH_2)_nOP(=O)(OR_4)_2$,
$(CH_2)_nO(CH_2)_nP(=O)(OR_4)_2$,
$CF_3$,
$CH_2CF_3$,
$OCF_3$, and
$OCH_2CF_3$;
in which phenyl, naphthyl, heteroaryl, cycloalkyl, and heterocyclyl are optionally substituted with one to three substituents independently selected from halogen, hydroxy, $C_{1-4}$ alkoxy, $C_{3-6}$ cycloalkyl, and $C_{1-4}$ alkyl wherein alkyl is optionally substituted with hydroxy or one to three fluorines; and wherein any methylene ($CH_2$) carbon atom in $R^3$ is optionally substituted with one to two groups independently selected from fluorine, hydroxy, and $C_{1-4}$ alkyl optionally substituted with one to five fluorines; or two substituents when on the same methylene ($CH_2$) group are taken together with the carbon atom to which they are attached to form a cyclopropyl group;
each $R^4$ is independently selected from the group consisting of
hydrogen,
$C_{1-6}$ alkyl,
$(CH_2)_m$-phenyl,
$(CH_2)_m$-heteroaryl,
$(CH_2)_m$-naphthyl, and
$(CH_2)_mC_{3-7}$ cycloalkyl;
wherein alkyl, phenyl, heteroaryl, and cycloalkyl are optionally substituted with one to three groups independently selected from halogen, $C_{1-4}$ alkyl, and $C_{1-4}$ alkoxy, wherein alkyl and alkoxy are optionally substituted with one to five fluorines; or two $R^4$ groups together with the atom to which they are attached form a 4- to 8-membered mono- or bicyclic ring system optionally containing an additional heteroatom selected from O, S, and $NC_{1-4}$ alkyl;
each $R^5$ is independently selected from the group consisting of
$C_{1-6}$ alkyl,
$C_{2-4}$ alkenyl,
$(CH_2)_nOR^4$,
$(CH_2)_n$-phenyl,
$(CH_2)_n$-naphthyl,
$(CH_2)_n$-heteroaryl,
$(CH_2)_n$-heterocyclyl,
$(CH_2)_nC_3$-7 cycloalkyl, halogen,
$(CH_2)_nN(R^4)_2$,
$(CH_2)_nC{\equiv}N$,
$(CH_2)_nCO_2R^4$,
$(CH_2)_nOC(O)R^4$,
$(CH_2)_nCOR^4$,
$NO_2$,
$(CH_2)_nNR^4SO_2R^4$
$(CH_2)_nSO_2N(R^4)_2$,
$(CH_2)_nS(O)_pR^4$,
$(CH_2)_nNR^4C(O)N(R^4)_2$,
$(CH_2)_nC(O)N(R^4)_2$,
$(CH_2)_nC(O)N(OR^4)R^4$,
$(CH_2)_nC(O)N(NH_2)R^4$,
$(CH_2)_nC(O)NR^4NC(O)R^4$;
$(CH_2)_nNR^4C(O)R^4$,
$(CH_2)_nNR^4CO_2R^4$,
$(CH_2)_nP(=O)(OR_4)_2$,
$(CH_2)_nOP(=O)(OR_4)_2$,
$(CH_2)_nO(CH_2)_nP(=O)(OR_4)_2$,
$O(CH_2)_nC(O)N(R^4)_2$,
$CF_3$, CH₂CF₃,
OCF₃, and
OCH₂CF₃;

in which phenyl, naphthyl, heteroaryl, cycloalkyl, and heterocyclyl are optionally substituted with one to three substituents independently selected from halogen, hydroxy, $C_{1-4}$alkoxy, $C_{1-4}$ alkylsulfonyl, $C_{3-6}$ cycloalkyl, and $C_{1-4}$ alkyl wherein alkyl is optionally substituted with hydroxy, carboxy, or one to three fluorines; and wherein any methylene (CH₂) carbon atom in R⁵ is optionally substituted with one to two groups independently selected from fluorine, hydroxy, and $C_{1-4}$ alkyl optionally substituted with one to five fluorines; or two substituents when on the same methylene (CH₂) group are taken together with the carbon atom to which they are attached to form a cyclopropyl group;

R⁶, R⁷, R⁸, R⁹, R¹⁰, R¹¹, and R¹² are each independently hydrogen or $C_{1-3}$ alkyl, wherein alkyl is optionally substituted with one to three substituents independently selected from fluorine and hydroxyl;

each n is independently 0, 1 or 2;
each m is independently 0, 1, or 2; and
p is 0, 1, or 2.

2. The compound of claim 1 of structural formula Ia having the indicated absolute stereochemical configuration at the stereogenic carbon atom marked with an *:

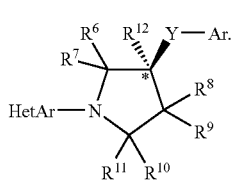

(Ia)

3. The compound of claim 2 wherein Y is O.
4. The compound of claim 3 wherein HetAr is 2-thiazolyl or 1,3,4-thiadiazol-2-yl monosubstituted at the C-5 position of the thiazole or 1,3,4-thiadiazole ring with R⁵.
5. The compound of claim 3 wherein Ar is phenyl or pyridyl optionally substituted with one to three R³ substituents.
6. The compound of claim 3 wherein Ar is phenyl or pyridyl optionally substituted with one to three R³ substituents, and HetAr is 2-thiazolyl or 1,3,4-thiadiazol-2-yl monosubstituted at the C-5 position of the thiazole or 1,3,4-thiadiazole ring with R⁵.
7. The compound of claim 1 wherein R⁶, R⁷, R⁸, R⁹, R¹⁰, R¹¹, and R¹² are hydrogen.
8. The compound of claim 1 wherein each R³ is independently selected from the group consisting of halogen, $C_{1-4}$ alkyl, trifluoromethyl, $C_{1-4}$ alkylsulfonyl, cyano, and $C_{1-4}$ alkoxy.
9. The compound of claim 1 wherein each R⁵ is independently selected from the group consisting of:
halogen,
cyano,
C(O)N(R⁴)₂,
C(O)R⁴,
CO₂R⁴,
CH₂OR⁴, wherein CH₂ is optionally substituted with one to substituents independently from hydroxy, fluorine, and methyl,
NR⁴C(O)R⁴,
SO₂N(R⁴)₂, and
heteroaryl which is selected from the group consisting of 1,2,4-oxadiazol-3-yl, 1,2,4-oxadiazol-5-yl, 1,3,4-oxadiazol-2-yl, 2-thiazolyl, and 2H-tetrazol-5-yl, wherein heteroaryl is optionally substituted with one to two substituents independently selected from halogen, hydroxy, $C_{1-4}$ alkoxy, $C_{3-6}$ cycloalkyl, and $C_{1-4}$ alkyl wherein alkyl is optionally substituted with hydroxy or one to three fluorines.

10. The compound of claim 2 of structural formula (Ib) having the indicated absolute stereochemical configuration at the stereogenic carbon atom marked with an **:

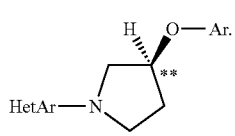

(Ib)

11. The compound of claim 10 wherein Ar is phenyl optionally substituted with one to three R³ substituents and HetAr is 2-thiazolyl or 1,3,4-thiadiazol-2-yl monosubstituted at the C-5 position of the thiazole or 1,3,4-thiadiazole ring with R⁵;

each R³ is independently selected from the group consisting of halogen, $C_{1-4}$ alkyl, trifluoromethyl, $C_{1-4}$ alkylsulfonyl, cyano, and $C_{1-4}$ alkoxy; and each R⁵ is independently selected from the group consisting of
halogen,
cyano,
C(O)N(R⁴)₂,
C(O)R⁴,
CO₂R⁴,
CH₂OR⁴, wherein CH₂ is optionally substituted with one to substituents independently from hydroxy, fluorine, and methyl,
NR⁴C(O)R⁴,
SO₂N(R⁴)₂, and
heteroaryl which is selected from the group consisting of 1,2,4-oxadiazol-3-yl, 1,2,4-oxadiazol-5-yl, 1,3,4-oxadiazol-2-yl, 2-thiazolyl, and 2H-tetrazol-5-yl, wherein heteroaryl is optionally substituted with one to two substituents independently selected from halogen, hydroxy, $C_{1-4}$ alkoxy, $C_{3-6}$ cycloalkyl, and $C_{1-4}$ alkyl wherein alkyl is optionally substituted with hydroxy or one to three fluorines.

12. The compound of claim 11 wherein R⁵ is heteroaryl optionally substituted with one to three substituents independently selected from halogen, hydroxy, hydroxymethyl, $C_{1-3}$ alkyl, trifluoromethyl, and $C_{1-3}$ alkoxy.

13. The compound of claim 12 wherein heteroaryl is 1,3,4-oxadiazol-2-yl or 1,2,4-oxadiazol-3-yl each of which is optionally substituted with one substituent independently selected from halogen, hydroxy, hydroxymethyl, $C_{1-3}$ alkyl, trifluoromethyl, and $C_{1-3}$ alkoxy.

14. The compound of claim 13 which is selected from the group consisting of:
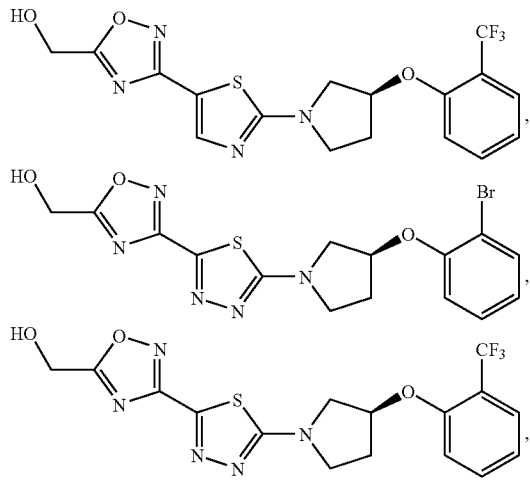
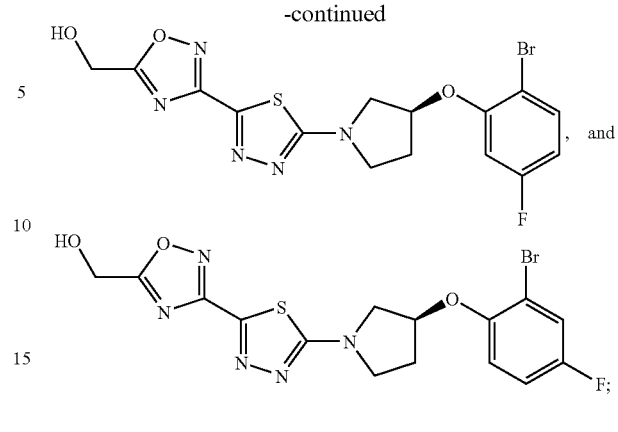
or a pharmaceutically acceptable salt thereof.
15. A pharmaceutical composition comprising a compound in accordance with claim 1 in combination with a pharmaceutically acceptable carrier.
* * * * *

UNITED STATES PATENT AND TRADEMARK OFFICE
CERTIFICATE OF CORRECTION

PATENT NO. : 7,754,745 B2 Page 1 of 1
APPLICATION NO. : 12/227549
DATED : July 13, 2010
INVENTOR(S) : Chun Sing Li and Yeeman K. Ramtohul It is certified that error appears in the above-identified patent and that said Letters Patent is hereby corrected as shown below:

On the Title Pg, Item (74), Atty, Agent or Firm: delete "Philippe L. Derette".

On the Title Pg, Item (74), Atty, Agent or Firm: add -- Philippe L. Durette --.

Signed and Sealed this

Seventh Day of September, 2010

David J. Kappos
*Director of the United States Patent and Trademark Office*